(12) United States Patent
Garyantes

(10) Patent No.: US 6,565,813 B1
(45) Date of Patent: May 20, 2003

(54) VIRTUAL WELLS FOR USE IN HIGH THROUGHPUT SCREENING ASSAYS

(75) Inventor: Tina Garyantes, Warren, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/601,708
(22) PCT Filed: Feb. 3, 1999
(86) PCT No.: PCT/US99/02300
§ 371 (c)(1), (2), (4) Date: Aug. 12, 2000
(87) PCT Pub. No.: WO99/39829
PCT Pub. Date: Aug. 12, 1999

Related U.S. Application Data
(60) Provisional application No. 60/073,697, filed on Feb. 4, 1998, and provisional application No. 60/087,721, filed on Jun. 2, 1998.

(51) Int. Cl.⁷ .................................................. B01L 3/00
(52) U.S. Cl. .................... 422/102; 422/100; 435/288.3; 435/288.4
(58) Field of Search ............................... 422/100, 102, 422/99, 104; 435/288.3, 288.4; 359/398

(56) References Cited

U.S. PATENT DOCUMENTS

| | | | |
|---|---|---|---|
| 3,736,042 A | * 5/1973 | Markovits et al. | 356/246 |
| 4,741,619 A | 5/1988 | Humphries et al. | |
| 4,798,706 A | * 1/1989 | Brigati | 206/84 |
| 5,041,266 A | 8/1991 | Fox | |
| 5,229,163 A | 7/1993 | Fox | |
| 5,424,186 A | * 6/1995 | Fodor et al. | 435/49 |
| 5,545,531 A | * 8/1996 | Rava et al. | 435/6 |

FOREIGN PATENT DOCUMENTS

| | | |
|---|---|---|
| EP | 9 402 718 A | 12/1990 |
| WO | WO 94/27719 | 12/1994 |
| WO | WO 97/22875 | 6/1997 |
| WO | WO 98/03257 | 1/1998 |

OTHER PUBLICATIONS

Scientific Apparatus Catalog 80, VWR Scientific, Inc., p. 1228, 1980.*

Matsuda et al., "Microfabricated Surface Designs for Cell Culture and Diagnosis", *ASAIO Journal*, 1994, pp. M594–M597.

Meier–Ewert et al., "An automated approach to generating expressed sequence catalogues", *Nature*, vol. 361, pp. 375–376, 1993.

(List continued on next page.)

*Primary Examiner*—Alexander Markoff
(74) *Attorney, Agent, or Firm*—Van Dyke & Associates, P.A.

(57) ABSTRACT

Microtiter-like plates containing virtual wells formed by an arrangement of relatively hydrophilic domains within relatively hydrophobic fields are provided. Assay mixtures are confined to the hydrophilic domains of the virtual wells by the edges of the hydrophobic fields. The use of virtual wells allows one to perform homogeneous and capture and wash high throughput screening assays with assay mixtures having volumes on the order of about 100 nl to 10 μl. Virtual wells also provide a means of easily moving fluids, which is particularly useful for simultaneous additions needed for kinetic studies and flash detection and washing. Methods for controlling evaporation during the dispensing of reagents as well as during incubation of high throughput screening utilizing microtiter-like plates containing virtual wells are also provided.

The present invention also provides an inexpensive, disposable device for transferring small volumes of an entire array of compounds from a first microtiter-like plate to a second microtiter-like plate, preserving the spatial arrangement of the compounds. Methods of manufacturing and using the device are also provided.

21 Claims, 14 Drawing Sheets

OTHER PUBLICATIONS

Kathlene A. Thompson, "Virtual Wells: Combinatorial Biology Demands Ultra–High–Throughput Screening", http://www.netsci.org/Science/Screening/feature04.html, Jan. 8, 1998, pp. 1–6.

You et al., "A miniaturized arrayed assay format for detecting small molecule–protein interactions in cells", *Chemistry & Biology*, pp. 969–975, Dec. 1997.

* cited by examiner

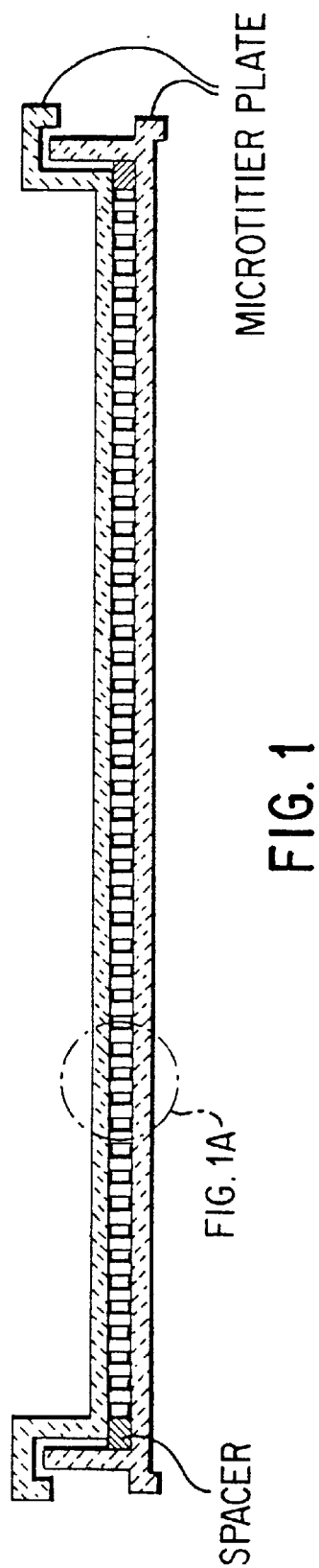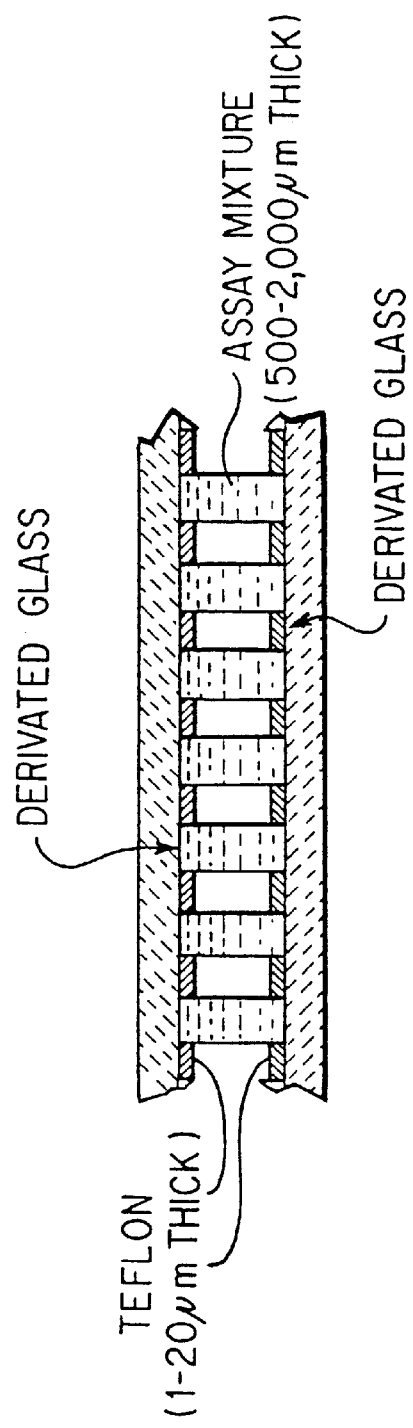

DROPLETS BEFORE CONTACT

DROPS IN CONTACT, FORMING NENISCUS

DROPLETS AFTER CONTACT

BEAD CAPTURED ON STREPTAVIDIN SURFACE

ADD DMSO AND PHOTOCLEAVE COMPOUND FROM SURFACE

ALIQUAT COMPOUND FOR ASSAY (OR MASS SPECTROSCOPY ANALYSIS)

ADD COMPOUND TO ASSAY

PLATE CELLS IN BULK MEDIA

REMOVE BULK MEDIA

ADD COMPOUND AND INCUBATE

REMOVE COMPOUND PLATE AND ADDED LYSIS BUFFER

CAPTURE mRNA

RT-PCR     DIRECT CHEMILUMINESCENT BINDING ASSAY     CHROMOGEN

VIRTUAL WELLS FOR USE IN HIGH THROUGHPUT SCREENING ASSAYS

CROSS-REFERENCE TO RELATED APPLICATIONS

The present application claims priority from U.S. Provisional Patent Application Serial No. 60/073,697, filed Feb. 4, 1998, and U.S. Provisional Patent Application Serial No. 60/087,721, filed Jun. 2, 1998, the disclosures of which are incorporated herein by reference, in their entireties.

STATEMENT REGARDING FEDERALLY-SPONSORED R&D

Not applicable

REFERENCE TO MICROFICHE APPENDIX

Not applicable

FIELD OF THE INVENTION

The present invention is directed to novel microtiter-like plates having a patterned arrangement of relatively hydrophilic domains within a relatively hydrophobic field that can be used in improved methods of high throughput screening of biological materials. The invention covers the plates and their uses for dispensing and moving fluids and for running high throughput screens. Also claimed are methods for controlling evaporation based on cooling the plates to the dew point during the dispense and limiting evaporation during incubation by providing a humidifying buffer in the plate design.

The present invention is also directed to a novel device that can be used to transfer fluids from a spatially ordered array of fluids at a first location to a second location, preserving the spatial relationships among the fluids. The device can be used as a top for the microtiter-like plates having a patterned arrangement of relatively hydrophilic domains within a relatively hydrophobic field. Methods of manufacturing and using the device are also provided.

BACKGROUND OF THE INVENTION

Current methods of drug discovery often involve assessing the biological activity (i.e., screening) of tens or hundreds of thousands of compounds in order to identify a small number of those compounds having a desired activity. The assays are generally carried out in multi-well tissue culture plates called microtiter plates. Microtiter plates are usually made of plastic, with the wells being formed by indentations in the bottom of the microtiter plate. For screening, commonly used microtiter plates have 96 individual wells, although the trend is to use higher density plates of 384, 864, 1536, 3456, and even 9600 wells. Current 96 well plates are made in a broad variety of shapes, colors, materials, and sizes, but they all have wells that hold volumes of at least tens of microliters, require individual dispensing of reagents into each well, and require individual washing of each well except in the case of select assays in filter bottom plates. Higher density plates typically have wells that hold lower volumes, but such plates are subject to more limitations in that few such plates are available with filters in the bottom and assay preformance is often compromised. Thus, for plates with more than 384 wells, it is currently not feasible to run biological assays requiring a capture and wash step and moving fluids into and out of the narrow wells of such plates requires very precise pipetting.

In general, it is desirable to utilize microtiter plates having the largest possible number of wells per plate and the smallest possible volume per well, in order to maximize the throughput and minimize the mechanical complexity of high throughput screening operations. In addition, the use of smaller volumes per assay is desirable for a number of reasons: conservation of scarce biological and chemical materials, more efficient use of reagents, ability to run assays on primary cells, ability to develop assays faster due to requiring less reagent purification, fewer plates needed to run a given number of assays and thus fewer handling problems and less storage space needed.

While it is desirable to decrease the size of wells in current microtiter plates, there are problems associated with doing so, including, e.g., difficulty pipetting fluids into confined spaces, inadequate and slow mixing, difficulty effecting separations, rapid evaporation times, and limited signal strength during measurement.

It would be highly desirable to have microtiter plates containing as large a number of wells as possible that hold on the order of 10 nl to 10 $\mu$l of assay mixture; that are easy to pipette into; facilitate fluid transfer; minimize mixing time; and allow for easy separations and washing. The present invention provides such plates and methods of their use. Importantly, the design of the plates facilitates fluid transfer, making them also a pseudopipetting device.

Another limitation to the miniaturization of current screening systems is that of evaporation of the reagents during dispensing of the reagents. This problem is generally minimized by pipetting in humidified environments or floating a non-miscible, non-volatile solvent on top of the pipetted component. The humidified environment is difficult to regulate, corrosive to automated equipment, and messy due to condensation. It is difficult to find a truly non-miscible solvent to float on the broad variety of chemicals typically tested in a pharmaceutical screen. The present invention provides two methods for controlling evaporation, one based on pipetting assay components at the dew point that is easy to regulate, non corrosive, clean, and practical and the second based on having a humidifying buffer integral to the plate.

The problem of dispensing an array of small volumes containing compounds of interest in a functional form for screening has been a major obstacle toward miniaturization. In the past, the problem of dispensing small volumes containing compounds of interest into or out of the wells of microtiter plates has been accomplished by use of metal pins that need to be washed after each use (such as on the BioMek 2000 High Density Replicator (HDR) tool, see, e.g., Brandt, 1997, J. Biomolec. Screen. 2:111–116); or by pin replicators (such as the pin replicator made by V&P Scientific, Inc., 1997, J. Biomolec. Screen. 2: 118) or by aspirating a relatively large volume (usually at least 100 nl and generally at least a few $\mu$l of solution) with a low volume pipetter such as the Packard piezoelectric pipetter or Cartesian's solenoid based pipetter. The prior art pin tools or pin replicators are not ideal because they need to be washed (leading to possible contamination and loss of time), work at large volumes, do not have the accuracy needed, or are too expensive. In addition, the prior art pin tools do not act as a reusable lid for the storage of low volume (1–2 $\mu$l) compound arrays.

Pipetters, such as those listed above, also have their drawbacks. They are very slow and, like the prior art pins, they also need to be washed, leading to possible contamination and loss of time. The pipetters also require significant dead volumes in the 10s if not 1,000s of nanoliters. In addition, the pipetters, like the prior art pin tools, do not act as lids.

Given the difficulties involved in dispensing and removing reagents or compounds from the wells of microtiter plates, there is a clear need for a device that allows one to remove and then dispense small volumes of reagents from multiple wells simultaneously, without the need to wash the device between uses and without the need to use pipetters with their inherent drawbacks. In particular, such a device that can be activated manually and stabilizes the reagents or compounds for storage would be ideal.

SUMMARY OF THE INVENTION

The present invention provides microtiter-like plates containing "virtual wells." Virtual wells could be any surface modification such as protrusions or slight indentations (e.g., having a depth of between 0.5 nm to 500 μm, preferably about 3 nm to about 200 μm, more preferably about 10 nm to about 100 μm, and even more preferably about 10 nm to about 50 μm), as well as chemical modifications, binding sites, or other discontinuities present in slight indentations, on the plate surface that orders or retains fluid drops into a defined spatial array. Typically, the virtual wells are formed by an arrangement of relatively hydrophilic domains within relatively hydrophobic fields. Solvated samples (compounds) and assay reagents are confined to the more hydrophilic domains of the virtual wells by the edges of the more hydrophobic fields. The use of virtual wells allows one to run high throughput screening assays that require the capture and washing of an assay component prior to reading, as well as assays simply requiring the mixing of components and reading, with assay mixtures having volumes on the order of about 10 nl to 10 μl. The virtual wells can also be used to effect near simultaneous addition or subtraction of fluid from all wells in a virtual well microtiter-like plate to enable screening fast kinetic and flash reactions. The virtual wells allow one to repeatedly transfer a known volume from each well of a spatially defined array of solutions into a second array in Ia single step and to precisely aliquot small volumes of compounds or reagents to multiple assays. The present invention also provides a means for controlling evaporation and providing a reproducible optical path. The present invention also includes methods of high throughput screening utilizing microtiter-like plates containing virtual wells.

The present invention also provides an inexpensive, disposable device for transferring small volumes of an entire array of compounds from a first microtiter-like plate to other microtiter-like plates multiple times, preserving the spatial arrangement of the compounds without risking contamination of samples or requiring excessive washing time. Methods of manufacturing and using the device are also provided.

BRIEF DESCRIPTION OF THE DRAWINGS

FIGS. 1 and 1A depict a side view of a typical arrangement of a microtiter-like plate containing "virtual wells." In this case, the microtiter-like plate has a top and bottom, each of which contains hydrophilic domains within a hydrophobic field. The aqueous assay mixtures are held in the virtual wells between the top and bottom of the microtiter-like plate due to the hydrophobic nature of the TEFLON® composite material, such as TEFLON® beads in a matrix of supporting material, which prevents the assay mixtures from spreading over the entire surfaces of the top and bottom. In the magnified view of the figure, the seven columns represent seven columns of fluid held in place by the opposing virtual wells on the top and bottom surfaces, each of which could contain the same or a separate assay mixture. The use of TEFLON® composite material, such as TEFLON® beads in a matrix of supporting material, as the hydrophobic field and derivatized glass as the hydrophilic domains is meant to be illustrative only. The invention can be practiced with a wide variety of materials making up the hydrophobic fields and the hydrophilic domains or other surface modifications acting as the virtual wells.

FIG. 2A. The two plates shown each have a sample in a virtual well on the surface of the plate facing the other plate. The virtual well is formed by a small hydrophilic domain within a large hydrophobic field. The plates are aligned so that the virtual wells come into close proximity when the plates are moved together.

FIG. 2B depicts the process of combining assay mixtures by moving the plates into close proximity. The dark colored solution on the top plate is thereby mixed with the light colored solution on the bottom plate. If desired, following mixing, the plates can be moved apart, resulting in two plates, each having a virtual well containing the mixed solution. For clarity, a single virtual well on each plate is shown. Of course, in actual practice, each plate would generally have many virtual wells. Also for clarity, side walls are not shown. In actual practice, the alignment of one plate to the other could be assured by the use of side walls

FIG. 3A shows how the present invention can be used to transfer fluid from one plate (the top plate) to another (the bottom plate). The top plate does not contain hydrophilic domains; thus the aqueous fluid beaded on the hydrophobic surface of the top plate will transfer to the hydrophilic domains within hydrophobic fields on the bottom plate when the two plates are moved into close proximity. The same procedure can be done, albeit with some partitioning of fluid to the top plate upon removal, by using a hydrophilically patterned top slide.

FIG. 3B shows the addition of fluid to the bottom plate from the top plate. The fluid transfers because the top plate lacks the hydrophilic areas of the bottom plate. The same procedure can be done, albeit with some partitioning of fluid to the top plate upon removal, by using a hydrophilically patterned top slide.

FIG. 3C shows how a top plate having smaller hydrophilic areas than the bottom plate can be used to remove part of the fluid from the virtual wells of the bottom plate. The volume transferred from one plate to the other is a strong function of the relative diameters of the virtual wells and a weaker function of the volume in the bottom well, the orientation of the plate, the particular fluid being moved, and the spacing between the two plates. Multiple equal volume aliquots can be taken from the set of wells by proper adjustment of the aforementioned parameters.

FIG. 4A shows a combinatorial bead bound to a well with a streptavidin surface. For the purposes of illustration, the bead's surface contains a compound from a combinatorial library that is tethered to the bead by a photocleavable linker. The bead could be bound to the surface by any of a host of chemical or physical binding or capturing methodologies. The compounds could be attached to the bead or other solid support by any photocleavable, chemical, or physical linker.

FIG. 4B shows the process of releasing the compound from the bead by photocleavage. The bead is coated with a small amount of DMSO and the compound is released from the bead by photocleavage. Photocleavage in DMSO is shown by way of illustration; the compound could just as easily be cleaved chemically by solution or vapor phase cleavage into many solvents. Photocleavage could also be done into many solvents. The bead could be cleaved in a different solvent from that used to transfer a portion of the cleaved material to the assay. In addition to DMSO, a wide range of organic solvents may be used for transfer. Such solvents need not be very hydrophilic; what is necessary is merely that such solvents be more hydrophilic than the hydrophobic fields.

FIG. 4C shows how a portion of the solubilized compound from the bead may be transferred to the virtual well of a second plate (top plate) by bringing the second plate into close proximity with the first plate. A small amount of solubilized compound is thus transferred to the virtual well. Since only part of the solution containing the compound is transferred, the bead can be used many times in this procedure. The top plate, now containing the compound in its virtual well, can be used for any assay in which it is desired to test the compound. Alternatively, the compound in the virtual well can be put through an analytical procedure such as, e.g., mass spectroscopy, atomic absorption, UV or IR spectroscopy, fluorescence, etc.

FIG. 4D shows the second plate from FIG. 4C following transfer of the compound to it. Although, for illustration here, the compound has come from a combinatorial bead, it could just as easily have come from a solution phase synthesis or any other source.

FIG. 4E shows how the compound in the small virtual well of the second plate can be added to an assay being carried out in the large virtual well of the bottom plate.

FIGS. 5A–E shows how the present invention can be used easily to assay for substances that have to be separated from the general assay mixture as, e.g., from cells in tissue culture. In this case, the substance is mRNA produced in response to a compound that the cells are exposed to.

FIG. 5A shows tissue culture cells that have been plated onto plates which contain virtual wells. The cells preferentially adhere to the hydrophilic domains of the virtual wells (which may be derivatized for cell culture) and not to the hydrophobic fields.

FIG. 5B shows the plate of FIG. 5A after the bulk of the tissue culture media has been taken off the plate. What remains are the cells within the virtual wells and a tiny amount of media surrounding the cells.

FIG. 5C shows the addition of a compound to the cells via the use of a second plate containing a virtual well in which the compound is present in a solution in the virtual well. The compound is thus transferred to the tissue culture media, exposing the cell to the compound. Following a period of incubation, the cells are lysed and their contents analyzed.

FIG. 5D shows the addition of lysis buffer to the cells by the use of a plate containing a virtual well containing lysis buffer.

FIG. 5E shows the use of another plate to spatially capture and remove the substance (in this case, mRNA) from the solution containing the lysed cells. The top plate, shown, has a virtual well which contains a material that selectively binds the mRNA. The plate could just as easily not be patterned with hydrophobic material. The top plate can then be washed and analyzed for the substance.

FIG. 6A shows a top view of the bottom of the microtiter-like plate, without the cover.

FIG. 6B shows a cross-section of a side view of the microtiter-like plate, with the cover in place.

FIG. 7A shows the results of four experiments that looked at the rate of evaporation from a glass slide of a 17 nl drop of water dispensed by the single tip BioChip piezo pipetter from Packard. The time to completely evaporate the drop is plotted as a function of the relative humidity at the drop. The relative humidity at the drop was calculated by dividing the grams of water a cubic meter of air can hold at the slide temperature by the multiple of the relative humidity in the chamber by the grams of water a cubic meter of air can hold at the chamber temperature. Any data plotted at 60 minutes means that it took more than one hour for the drop to evaporate.

FIG. 7B shows the same data as in FIG. 7A but in this case the x-axis is the difference in grams of water/cubic meter of air that can be held in the chamber versus at the drop surface.

FIG. 8 illustrates a process for making the transfer device of the present invention.

FIG. 9 illustrates the use of the device of the present invention.

FIG. 11A shows an embodiment of the device of the present invention where the device is a pin array in a lid for a microtiter-like plate containing virtual wells. FIG. 11B shows the pin array of the device where the faces of the pins have been coated with a photoresist. The photoresist protects the hydrophilic faces of the pins from subsequent treatment with a hydrophobic substance. FIG. 11C shows the pin array with photoresist after it has been coated with a hydrophobic material such as wax disolved in hexane. FIG. 11D shows a partial view of the finished pin array (after the photoresist has been removed) with hydrophilic tips and hydrophobic shafts. This configuration allows for repeated aliquoting from an array of solutions with minimal effect of sample volume in the stock solution.

FIG. 12A shows that, when plates contain virtual wells of the same size, the wells can become skewed due to typical sources of misalignment such as play between the two plates, resulting in less fluorescence being emitted. FIG. 12B shows that, when plates contain virtual wells of different size, with the smaller sized wells being on the side from which excitation comes, the fluorescence signal is constant, even if the plates are misaligned.

DETAILED DESCRIPTION OF THE INVENTION

Figure 2A:
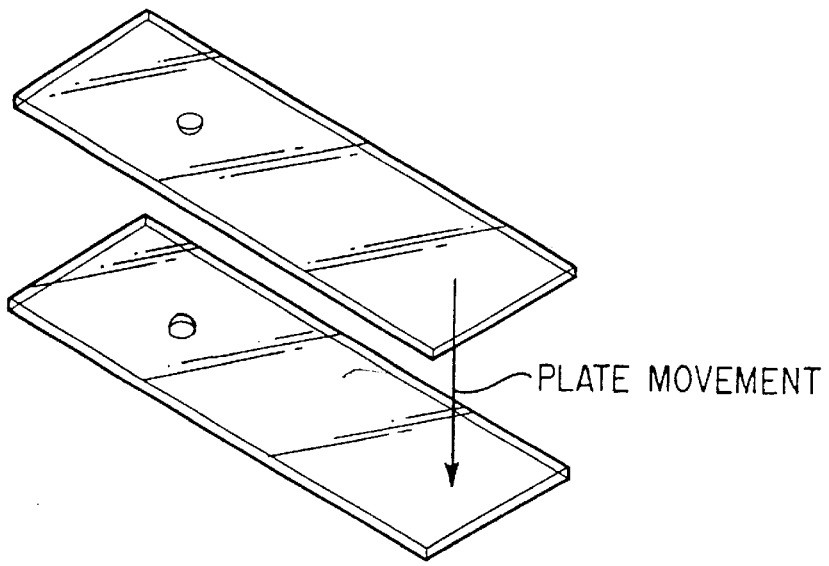
FIGS. 2A–B depicts a typical procedure for combining solutions using plates containing virtual wells where the plates are glass slides.

For the purposes of this invention:

"Close proximity" refers to the distance between two plates, at least one of which contains virtual wells, that is effective to limit evaporation, or to transfer, either completely or partially, a solution or component from one plate to another, or to mix a solution on one plate with a solution on another. Generally, such a distance will be from about 100 µm to 4,000 µm. One of skill in the art would recognize that the optimum distance is determined by the desire to limit evaporation and insure that the fluids do in fact touch for transfer while not squeezing the liquid out of the virtual wells. Because mixing is diffusion limited, the optimum distance for fast mixing will be such that the fluid shape most closely approximates a sphere without touching the fluid in an adjacent well. Another secondary consideration is to insure reproducible transfer volumes. This requires that the fluid in the well have limited contact with the hydrophobic field. (see FIG. 1). Spacers can aid in moving two plates into close proximity. Generally, spacers separating two plates can be from 100 µm to 4,000 µm thick.

"Close proximity" also refers to the distance between the faces of the pins of the device of the present invention and the wells of a microtiter-like plate that is effective to transfer, either completely or partially, fluid from the pins of the device to the wells of the plate or fluid from the wells of the plate to the pins of the device or to cover the plate with the device to limit evaporation and dust contamination. One of skill in the art would recognize that the optimum distance is determined by the desire to ensure that the fluids do in fact transfer while not squeezing the fluid out of the wells. Because mixing is diffusion limited, when it is desired to mix different fluids, the optimum distance for fast mixing will be such that the fluid shape most closely approximates a sphere without touching the fluid in an adjacent well. Another consideration is to ensure reproducible transfer volumes. Spacers can be employed between the device and the microtiter plate to ensure that the optimal distance is used. Generally, spacers can be from 100 µm to 4,000 µm thick.

"Spatial array" refers to an arrangement of fluids in a pattern, with each fluid in the pattern representing an element of the spatial array. For example, fluids filling the wells of a 96 well microtiter plate are present in a spatial array and the fluid in each well is an element of the spatial array. Fluids filling only some of the wells in a 96 well microtiter plate would also be present in a spatial array. In such spatial arrays, the fluids in each well can be the same or different. The fluids in an array can be pure, e.g., pure DMSO, pure $H_2O$, or they can be solutions of a compound or compounds, e.g., a 1M NaCl solution. The fluids can contain the same or different compounds dissolved therein. The fluids in an array can be mixtures of two or more fluids containing two or more compounds dissolved therein. Spatial arrays can have any number of elements; the above-described example of a 96 well microtiter plate is meant to be illustrative only. The elements of the spatial array can be arranged in any geometric pattern. One particularly useful spatial array is formed when the compounds that are members of a chemical library are present in the fluid in the wells of a microtiter plate. In a particular preferred embodiment, a different compound from a chemical or combinatorial library is present in each well.

"Diameter," when used to refer to the face of a pin where the face is circular, has its ordinary meaning with reference to circles. When used to refer to the faces of pins where the face is a square or other closed polygon, "diameter" means the length of a line connecting one side of the square or other closed polygon to the opposite side, where the line is perpendicular to both sides.

One spatial array is "similar" to another spatial array if the patterns of the elements of the arrays are physically superimposable upon each other. Thus, two spatial arrays are similar if the elements are geometrically arranged in such a way that they could be superimposed. For example, the wells of two standard 96 well microtiter plates (an 8×12 area of wells 9 mm center to center spacing) would be physically superimposable on each other and thus the wells of the two plates would represent similar spatial arrays.

Conventional microtiter plates contain wells that are formed by cylindrical, V, or cup-shaped indentations in the material forming the bottom plate of the microtiter plate. These wells generally have sidewalls and bottoms forming a depression in the bottom plate in which the samples are physically constrained under the influence of gravity. See, e.g., U.S. Pat. Nos. 5,229,161; 4,735,778; 4,770,856. Thus, it is the shape of the material making up conventional wells that confines the samples in those wells.

Figure 6A:
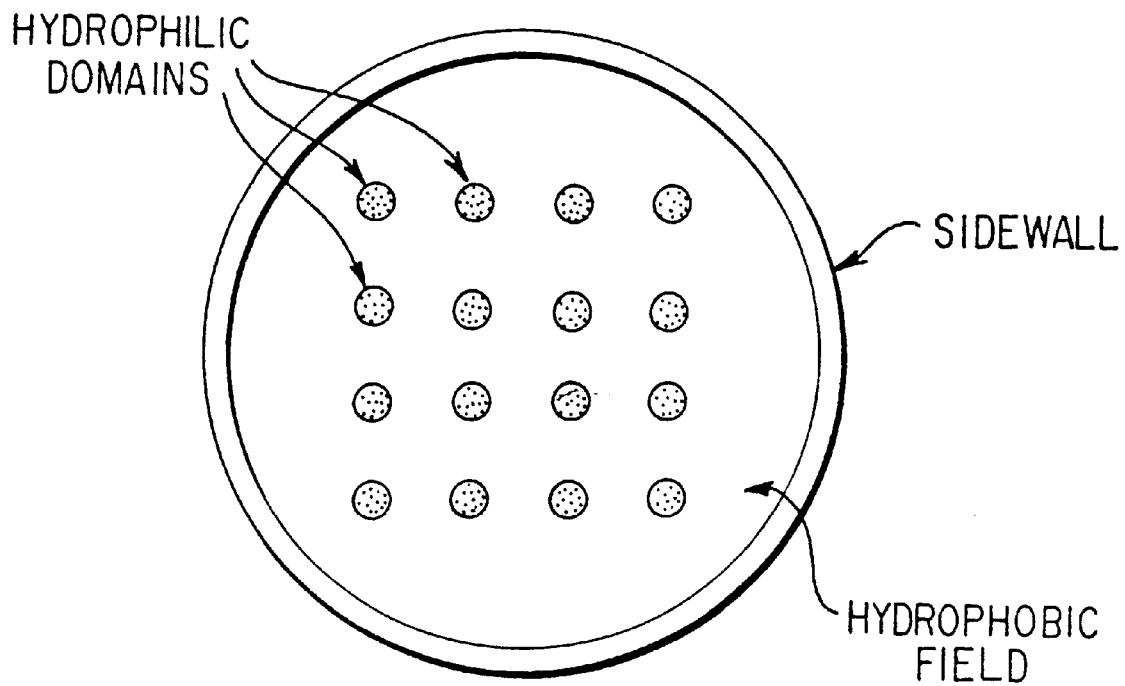
FIGS. 6A–B shows an embodiment of a microtiter-like plate having virtual wells on its bottom plate but not on its cover.
Figure 6B:
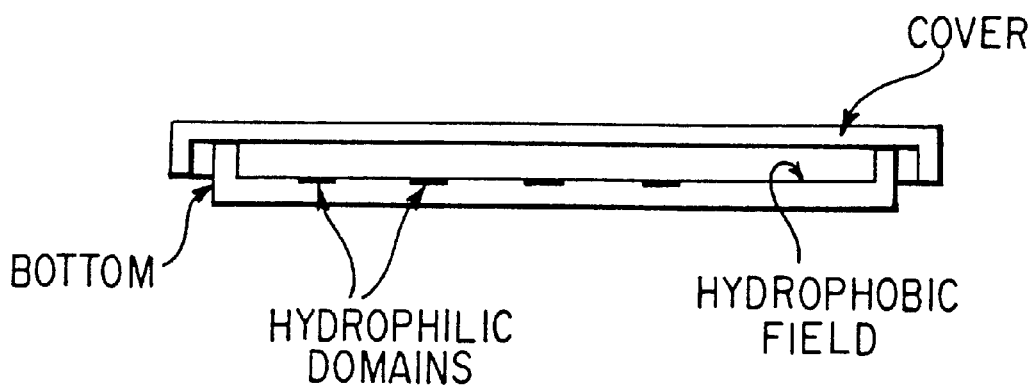

The present invention provides microtiter-like plates in which samples are confined to wells in an entirely different manner from the manner in which samples are confined in conventional microtiter plates. The present invention provides microtiter-like plates lacking the deep indentations found in conventional microtiter plates. The present invention provides microtiter-like plates having top plates and bottom plates with relatively flat, opposable surfaces of which at least one is patterned. The surfaces are patterned to have relatively hydrophilic domains within relatively hydrophobic fields so that a sample is physically constrained by surface tension to the more hydrophilic domains by the edges of the more hydrophobic fields. Thus, this arrangement of hydrophilic domains within hydrophobic fields creates "virtual wells." Alternatively, the "virtual wells" could be any surface modification that physically constrains a fluid by surface tension. These virtual wells provide a location in which samples can be confined. FIGS. 1 and 6 depict typical arrangements giving rise to virtual wells. The confined samples can be used in almost any known variety of high throughput screening assay or non-high throughput screening assay.

While the surfaces of plates containing virtual wells are generally flat to the eye or have gentle curvature, it will be understood by those skilled in the art that the hydrophilic domains may actually be extremely thin film-like areas that have been coated onto the surface of the hydrophobic fields. In some cases, the film-like areas may be a layer only a single molecule thick. In other cases, the layers may be somewhat thicker. Thus, the hydrophilic domains may actually be slightly raised compared to the hydrophobic fields. Similarly, in some embodiments, the hydrophobic fields may be extremely thin film-like areas that have been coated onto a hydrophilic surface. In no case, however, do the virtual wells consist of indentations with a depth of greater than about 1 mm, as in more conventional microtiter plates. For example, the embodiment shown in FIG. 1 can be viewed as representing a layer of polyfluorocarbon beads in a carrier matrix (viz., TEFLON® composite material [TEFLON® beads in a matrix of supporting material]) that has been deposited onto derivatized glass. The bead and carrier layer in FIG. 1 is about 20 $\mu$m thick. The process described herein that can be used to produce virtual wells generally results in virtual wells that are formed by hydrophobic fields lying on hydrophilic substrates where the surface of the hydrophobic field is raised about 0.5 nm to about 500 $\mu$m, preferably about 3 nm to about 200 $\mu$m, more preferably about 10 nm to about 100 $\mu$m, and even more preferably about 10 nm to about 50 $\mu$m, relative to the surface of the hydrophilic substrate, or where the virtual wells are hydrophilic domains lying on hydrophobic fields where the surface of the hydrophilic domains is raised about 0.5 nm to about 500 $\mu$m, preferably about 3 nm to about 200 $\mu$m, more preferably about 10 nm to about 100 $\mu$m, and even more preferably about 10 nm to about 50 $\mu$m, relative to the surface of the hydrophobic fields.

The present invention provides virtual containers comprising two surfaces, both of which contact at least one fluid that is formed into an array of droplets by virtue of modifications to the two surfaces. The modifications can be protrusions or slight indentations (e.g., having a depth of between 0.5 nm to 500 $\mu$m, preferably about 3 nm to about 200 $\mu$m, more preferably about 10 nm to about 100 $\mu$m, and even more preferably about 10 nm to about 50 $\mu$m), as well as chemical modifications, binding sites, or other discontinuities present in slight indentations. The droplets are not completely spatially confined by the combined surfaces, but rather at least part of the droplets is exposed to air (see, e.g., FIG. 1) or another gas or fluid. In some embodiments both surfaces contain modifications; in other embodiments, only one surface contains modifications. In some embodiments, both surfaces are modified and one surface is modified such that some or all of the modifications are substantially aligned with those of the companion surface.

In particular embodiments, the surfaces are held at a controllable distance, one from the other.

In particular embodiments, the interaction of the two surfaces results in substantial alignment of the modifications on one surface relative to the modifications on the second surface.

In particular embodiments, the interaction of the two surfaces results in the two surfaces being a controlled distance from each other.

In particular embodiments, the virtual containers comprise a first and second surface both of which surfaces contact at least one fluid that is formed into an array of droplets by virtue of modifications to the first surface; where the droplets are not completely spatially confined by the combined walls of the two surfaces, but rather at least part of each droplet is exposed to air; where the surfaces are held at a controllable distance, one from the other; and where the second surface is not modified in an array but is removable from the container.

In some embodiments, the second surface is used to augment the function of the first surface by adding or subtracting fluid from the array or the surrounding surface; by controlling evaporation; by capturing one or more components of the fluid in the array; by cleaning the first surface; by improving the performace of the containers for their ultimate use; or by speeding mixing.

In some embodiments, at least one surface is modified by pins, wells, holes, or chemical coatings, or etching which are used to define the fluid array or transfer all or part of the fluid array.

The containers may be used for performing or modifying chemical, biological, or cellular reactions, or physical changes within fluids, or any part there of.

Furthermore, the surface of the hydrophobic fields need not be completely flat. In certain embodiments, is is preferred that the surface be both hydrophobic and, at least at the microscopic level, rough. It is possible that, since roughness increases the surface area of the hydrophobic field, this results in an increase in the field's apparent hydrophobicity, leading to improved performance in some instances. One method of achieving a desired degree of roughness is to make the hydrophobic field from TELFON® beads, or other polyfluorocarbon or polyfluorocarbon-coated beads, or hydrocarbon or hydrocarbon-coated beads, in a carrier matrix. Such coatings can be obtained from commercial suppliers such as Erie Scientific (Portsmouth, N.H.), Cytonics, or Vellox. VELLOX® is 0.1 to 0.2 $\mu$m diameter fumed silica beads coated with a trimethyl siloxy coating in an acrylic copolymer resin layer. It is also expected that beads made from materials similar to TELON®, i.e, polyfluorocarbons, will be suitable. Generally, when beads are used to make the hydrophobic field, the beads should have a diameter of from about 0.05 $\mu$m to about 50 $\mu$m, preferably from about 0.075 $\mu$m to about 5 $\mu$m, and even more preferably from about 0.1 $\mu$m to about 0.3 $\mu$m. Possible carrier matrices are: adhesives, waxes, epoxies, acrylics, polymers, or polyvinyliden fluoride. Another method of making such hydrophobic fields is to modify a portion of an already rough surface such as ground or sintered glass. Roughness is characterized in millions of an inch (1 $\mu$m=39 millionths of an inch). Typically, surfaces that are rough to about 0.1–1 $\mu$m or 4 to 40 millionths of an inch are most desirable.

Assays using virtual wells are generally run in a microtiter-like plate complete with a lid or top plate so that evaporation is limited by the relatively tortuous path to the edge and up and over the sidewalls that the vapor would have to traverse while still allowing gas exchange for live cell assays. An incubator is used for longer incubations. A fluid buffer can be incorporated into the side or flat of a plate if greater control is needed. Fluid addition and removal can be done by moving the top and bottom plates into or out of close proximity. The use of a spacer between the top and bottom plates, as shown in FIG. 1, may aid in this process by fixing the distance of close proximity. Initial measurements indicate that the variance in amount of fluid added or removed under a range of conditions is about 6% and almost always less than 10%. Compounds or assay components can also be added by pipetting into the relatively hydrophilic domains. Capture assays can be run by immobilizing the capture reagent on either the top or bottom plate, touching the capture reagent to the other plate, incubating, and then washing the capture reagent by dipping, or by continuous or bulk washes.

In particular embodiments, rather than a top and bottom plate, a single plate is used in the assays. In such embodiments, samples in the virtual wells of the single plate form rounded beads rather than the columns shown in FIG. 1.

Plates containing the virtual wells of the present invention are easy to use and can be used in conjunction with a variety of automated analysis equipment suited for carrying out high throughput screening assays. Such equipment is described in, e.g., U.S. Pat. Nos. 5,670,113; 5,139,744; 4,626,684. Plates containing virtual wells can also be used with most imaging detectors such as phosphoimagers, InstantImager (Packard), Tundra (Research Imaging), Optical Imager (Packard), FluorImager (Molecular Dynamics), etc.. The small volumes of the virtual wells permit compound and reagent savings. Assays previously not feasible because of limited reagents or compounds can now be run in virtual wells. Plates containing virtual wells allow for storage space savings and lengthened robotic runs since fewer plates are needed for a given number of assays since more assays per plate can be run. Fewer plates also results in fewer mechanical failures of automated equipment used to handle the plates.

The number of virtual wells per plate can vary widely. Virtual wells are typically formed by hydrophilic domains having diameters of about 1 mm. Any convenient spacing of the hydrophilic domains is possible, although regular rectangular arrays, such as those forming the wells of conventional tissue culture plates, are preferred today due to automation compatibility. Particularly preferred arrangements are those in which two plates have virtual wells spaced in such a way that, when the plates are brought in close proximity, the virtual wells of one plate are aligned with the virtual wells of the other plate so that fluid can be transferred from one plate to the other or so that column-like virtual wells are formed between the plates. An example of such an arrangement, forming column-like virtual wells, can be seen in the top and bottom plates shown in FIG. 1. Volumes contained in virtual wells can vary widely but are generally between 10 nl to 10 $\mu$l, preferably from 100 nl to 5 $\mu$l, and more preferably from 500 nl to 2 $\mu$l.

In order to make plates having virtual wells, a variety of techniques can be used. Typically, a polyfluorocarbon containing substrate (e.g., TEFLON®) is silk-screened onto a glass surface. In some instances, it may be advantageous to silk-screen the hydrophobic material onto glass through a stiff (e.g., stainless steel) mesh rather than the more typical nylon or silk mesh and then optically align the glass to a frame.

Another possibility is to first make a dummy pattern of the array of hydrophilic domains on a hydrophilic surface with a photoresist, then coat the entire surface with a suitably hydrophobic material, and finally selectively "lift-off" the photoresist and overlying hydrophobic material to reveal the hydrophilic pattern. This method has been carried out by using a 1:200 solution of candle wax in hexane as the hydrophobic material. After lifting off the photoresist, the wax was cleanly patterned and water repellant.

Another method is to coat a hydrophobic surface with a hydrophilic material and then make a photoresist pattern for etching the hydrophilic material directly.

Other methods for making the plates can include just about any method where a relatively hydrophobic or relatively hydrophilic layer can be patterned on top of a contrasting relatively hydrophilic or relatively hydrophobic layer. These methods include, but are not limited to, stamping, silk screening, or printing of a hydrophobic material on a hydrophilic surface or vice versa; layering the two surfaces and then patterning the top layer to expose the bottom layer; or directionally masking the bottom layer while adding the top layer. Some typical methods include photolithography, silk screening, plasma etching, shadow chemical vapor deposition, or using films from the proofing industry.

Another possibility is to begin with a plate made from a hydrophobic material, e.g., glass or polystyrene. Upon this plate is placed a mask, the openings of the mask defining the arrangement of virtual wells desired on the surface of the plate. The surface of the plate is then exposed to an oxidation process. The result is a pattern of oxidized, hydrophilic domains upon the surface of the hydrophobic plate. Methods of oxidation are known. See, e.g., U.S. Pat. No. 5,229,163 and European Patent Application EP 074790, which teach a process of oxidizing hydrophobic plastics by exposing the plastic to electrons from an electron discharge means such as a corona discharge apparatus.

The present invention provides a novel plate containing a plurality of hydrophilic domains within a hydrophobic field wherein the hydrophilic domains are circular and have a diameter of from about 100 $\mu$m to about 2 mm. Preferably, the diameters are from about 200 $\mu$m to about 1.5 mm. Diameters of 1–1.5 mm are preferred for running biological assays and diameters of 200 $\mu$m to 1 mm are preferred for fluid transfer. The relatively hydrophilic domains are most easily considered to be circles but they can be of any shape.

In particular embodiments of the above-described novel plate, the plate is glass, the hydrophilic domains are derivatized glass, and the hydrophobic field is silk screened TEFLON® coating the glass plate. Since optical methods, e.g., fluorescence measurements, are used in many assays, it is often desirable that the plate be made of an optically transparent material. Glass is one possibility, as are light transmitting hydrophilic polymers such as polystyrene or TOPAZ or hydrophobic polymers such as polypropylene. If a hydrophobic material is used as the plate, then the surface of this material can form the hydrophobic fields with a hydrophilic material layered or dropped on top for hydrophilic domains, to form the virtual wells. If the plate is made of hydrophilic material, its surface can be coated with a hydrophobic substance to give the hydrophobic field. Optically transparent materials are only important for plates used during optical detection, otherwise black, opaque or translucent plates may be desirable for different applications such as epi-illumination or fluid transfers.

Figure 12A:
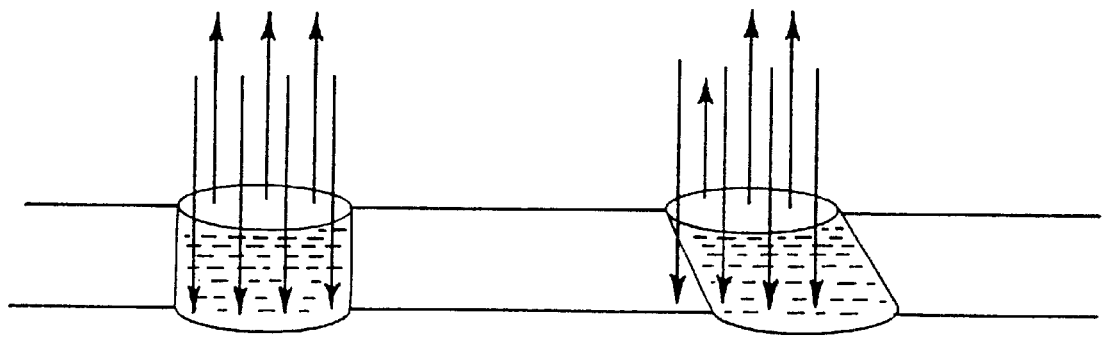
FIGS. 12A–B shows the optical path of light during fluorescence measurements when the virtual wells are in close proximity with the plate perfectly and imperfectly aligned, thus illustrating the advantage of having virtual wells with two different diameters for fluorescence assays. Both fluorescence excitation and imaging are from the top down in this figure. The arrows indicate fluorescence excitation passing down through the plates (arrows pointing down) and emission passing back up (arrows pointing up).
Figure 12B:
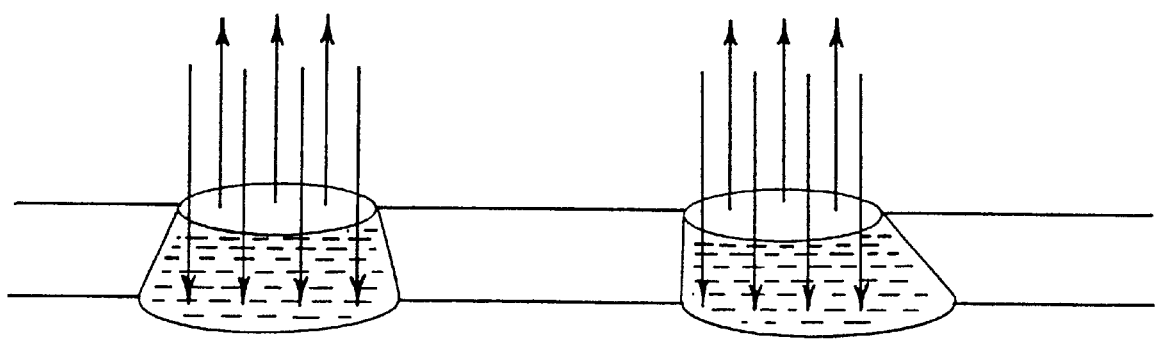
Figure 13:
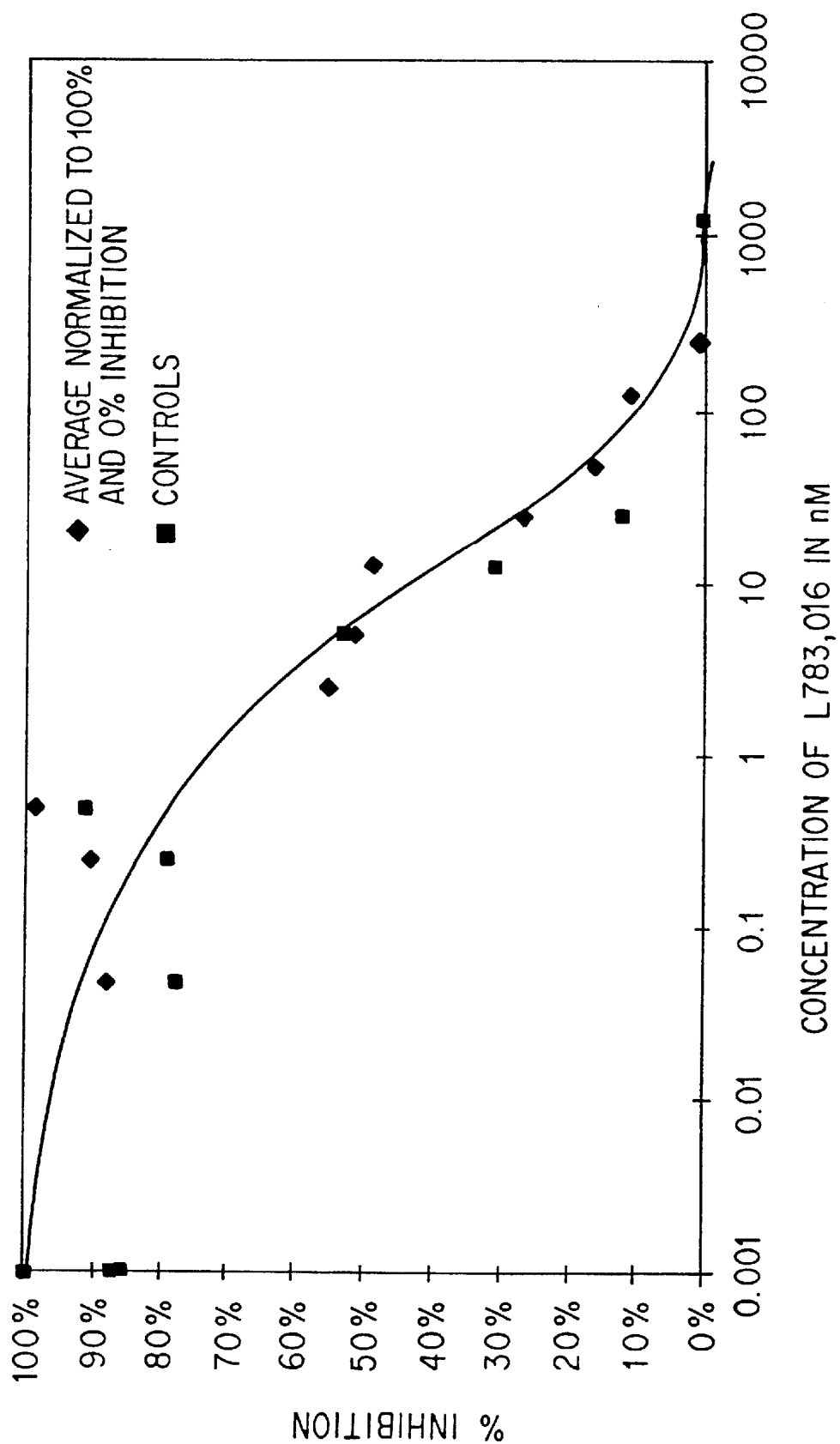
FIG. 13 shows the results of a assay for inhibition of PTP-1b using plates containing virtual wells.

When fluorescence detection is used, it is desirable that the diameters of the virtual wells on the top and bottom of the plates should be different. This difference allows for better definition of the imaged area (e.g., by allowing the integrated spot area imaged to be consistent across the plate) and minimizes imaging the edges of the fluid in the virtual wells, thus avoiding or minimizing assay variability. See FIG. 12. Differences in the diameters of the virtual wells on the top and bottom of the plates also permits for easier manufacturing of the plates since such differences increase the positional tolerances of the wells to within convenient manufacturing limits.

Optical detection methods such as fluorescence detection generally employ an excitation and an imaging step. The excitation and imaging steps can each be done through the top or through the bottom of a plate. When using virtual wells of different diameters in the top and bottom of a plate, it is desirable that the wells with the smaller diameter should be located on the part of the plate through which the excitation step first passes. For example, if one is exciting from the top down, then the excitation will first pass through the top of the plate. Therefore, the virtual wells of the top should be somewhat smaller than the virtual wells in the bottom. This will ensure that excitation of the edges of the fluid in the wells in the bottom is minimized.

The present invention provides a novel microtiter-like plate comprising:
  (a) a bottom having an upper surface comprising a plurality of virtual wells, said virtual wells being relatively hydrophilic domains within a relatively hydrophobic field;
  (b) a cover configured for enclosing said bottom.

In particular embodiments, said bottom comprises a sidewall or spacer and said top rests on said sidewall or spacer. In certain embodiments, the sidewall is a continuous upstanding sidewall along the perimeter of the bottom. In other embodiments the spacers are distributed along the inside of the lid so that the lid rests on the plate centered and at a controlled height by virtue of the spacers.

A typical example of the above-described novel microtiter-like plate is depicted in FIG. 6. In an alternative embodiment, there are virtual wells in the lower surface of the cover of the above-described microtiter-like plate, with or without opposing wells on the bottom plate. As with conventional microtiter plates, the overall shape of the plate can be rectangular, square, or circular.

In particular embodiments, the hydrophilic domains are typically selected from the group consisting of: plain glass, derivatized glass, silanized glass, glass with bio- and non-biopolymers absorbed, polystyrene and other plastics, Indium Tin Oxide and other metal oxides, gold and other metals, and ceramics. Derivatized glass is glass that has had its surface modified to be something other than $SiO_2$. The surface could be modified with proteins, nucleic acid, or other polymers absorbed.

In particular embodiments, the hydrophobic field is selected from the group consisting of: TEFLON®, various TEFLON®-like materials (e.g., polyfluorocarbons or perfluoropropene oxide) in carrier matrices such as epoxy with or without dyes or other materials added to absorb fluorescence. Other materials suitable for the hydrophobic field include waxes or oils (e.g. paraffin), hydrocarbons (e.g. polyethylene), silanizing agents (e.g. chlorodimethyl octyl silane), hydrophobic polymers such as polypropylene, and bifunctional materials that may bind ionically or covalently to the glass. A preferred embodiment employs a hydrophobic field that is both hydrophobic and, at least at the microscopic level, rough. One method of achieving a desired degree of roughness is to make the hydrophobic field from polyfluorocarbon or polyfluorocarbon-coated beads, or hydrocarbon or hydrocarbon-coated beads, in a carrier matrix. The coatings for such beads can be obtained from commercial suppliers such as Erie Scientific (Portsmouth, N.H.) or Cytonics or Vellox. VELLOX® coating is 0.1 to 0.2 $\mu$m diameter fumed silica beads coated with a trimethyl siloxy coating in an acrylic copolymer resin layer.

In a particular embodiment, the cover has a sidewall and the separation between the cover and the bottom is 100 $\mu$m to 4,000 $\mu$m, as determined by the different heights of the bottom and cover sidewalls. In another embodiment, the plate comprises a spacer that can vary in height so that the distance between the bottom and cover of the plate is not determined by the height of the sidewalls but rather is determined by the height of the spacer.

The present invention provides methods of high throughput screening that employ the above-described novel microtiter-like plate.

The present invention also provides a novel microtiter-like plate comprising:
  (a) a bottom having an upper surface comprising a plurality of virtual wells, said virtual wells being hydrophilic domains within a hydrophobic field, and a continuous upstanding sidewall along the perimeter of the bottom;
  (b) a top having a lower surface comprising a plurality of virtual wells, said top configured for enclosing said bottom by resting on said sidewall;
  wherein said plurality of virtual wells of said bottom and said plurality of virtual wells of said top are present in an arrangement such that column-like virtual wells are formed between said bottom and said top when said bottom and said top are in close proximity.

A typical example of the above-described novel microtiter-like plate is depicted in FIG. 1. As with conventional microtiter plates, the overall shape of the plate can be rectangular, square, circular, or any other convenient shape. In particular embodiments, the above-described novel microtiter-like plate has a lowered top that is not patterned but that touches the bottom or has a top that is lowered but does not touch the bottom. In yet other embodiments, the novel microtiter-like plate could be not patterned but the top could be patterned or not patterned but have been used previously with a patterned bottom plate. In a variant of the invention, the bottom does not contain a sidewall but the top does.

In a particular embodiment, the spacing between plates is about 1,000 $\mu$m, although there is really no fundamental restriction on the spacing other than convenience. In particular embodiments, the sidewall is of a height such that when the top is resting on the sidewall, then the upper surface of the bottom and the lower surface of the top are in close proximity. In another embodiment, the plate comprises a spacer that can vary in height so that the distance between the bottom and top of the plate is not determined by the height of the sidewall but rather is determined by the height of the spacer.

In particular embodiments, the hydrophilic domains are selected from the group consisting of: plain glass, derivatized glass, silanized glass, glass with bio- and non-biopolymers absorbed, polystyrene and other plastics, Indium Tin Oxide and other metal oxides, gold and other metals, and ceramics.

In particular embodiments, the hydrophobic field is selected from the group consisting of: TEFLON®, various TEFLON®-like materials (e.g., polyfluorocarbons or perfluoropropene oxide) in carrier matrices such as epoxy with or without dyes or other materials added to absorb fluorescence or provide other desirable properties such as advantageous adhesion, binding, or viscosity. Other materials suitable for the hydrophobic field include waxes or oils (e.g. paraffin), hydrocarbons (e.g. polyethylene), silanizing agents (e.g. chlorodimethyl octyl silane), hydrophobic polymers such as polypropylene, and bifunctional materials that may bind ionically or covalently to the glass. A preferred embodiment employs a hydrophobic field that is both hydrophobic and, at least at the microscopic level, rough. One method of achieving a desired degree of roughness is to make the hydrophobic field from polyfluorocarbon or polyfluorocarbon-coated beads, or hydrocarbon or hydrocarbon-coated beads, in a carrier matrix. The coatings for such beads can be obtained from commercial suppliers such as Erie Scientific (Portsmouth, N.H.) or Cytonics or Vellox. VELLOX® coating is 0.1 to 0.2 $\mu$m diameter fumed silica beads coated with a trimethyl siloxy coating in an acrylic copolymer resin layer.

The present invention provides methods of high throughput screening that employ the above-described novel microtiter-like plate.

The present invention provides a method of screening (either high throughput or non-high throughput) comprising:

(a) providing a plurality of compounds suspected of having a preselected biological activity, said compounds being present in solutions;

(b) dispensing the plurality of compounds into a plurality of virtual wells on a plate, said virtual wells being hydrophilic domains within a hydrophobic field;

(c) determining whether said compounds in said virtual wells possess said biological activity.

Alternatively, an additional step can be added between steps (b) and (c) where the plate and lid are repeatedly separated and brought back together so as to speed mixing.

In particular embodiments, the compounds are present in DMSO or DMSO mixed with a second solvent such as water or MeOH.

Cell-based screening assays that are currently known in the art can generally be adapted to be run in plates containing virtual wells. Thus, the present invention provides methods of screening to identify a compound capable of modulating a preselected biological activity exhibited by cells comprising:

(a) providing cells in the virtual wells of a microtiter-like plate;

(b) exposing the cells to a compound or collection of compounds suspected of being capable of modulating the preselected biological activity to be exhibited by the cells;

(c) determining whether the preselected activity has been modulated.

In particular embodiments, the cells in each virtual well are exposed to one or a small number of the compounds of the collection and individual wells containing the cells that exhibit the preselected biological activity are identified.

The preselected biological activity can be any assayable variable commonly used in the art, for example: changes in membrane potential of the cells; increases or decreases in metabolites or ions such as ATP, cAMP, cGMP, phospholipids, calcium, etc.; changes in the transcription of certain genes; changes in fluorescent or chemiluminescent behaviour; changes in pH; changes in enzymatic activity; changes in the activity of receptor proteins; changes in the activity of ion channels; changes in the translational control of certain mRNAs; changes in the translocation of certain proteins into or out of subcellular locations; cell growth or inhibition of growth; pigment dispersion or aggregation; antibody binding; etc.

For use in methods such as those described above, the present invention provides a combination of microtiter-like plates containing virtual wells where the virtual wells contain cells. The cells in the microtiter-like plates and in the above described method may be prokaryotic or eukaryotic, including but not limited to, bacteria such as *E. coli*, fungal cells such as yeast, mammalian cells including, but not limited to, primary cells and cell lines of human, bovine, porcine, monkey and rodent origin, and insect cells including but not limited to Drosophila and silkworm derived cell lines. Cell lines derived from mammalian species which are suitable and which are commercially available, include but are not limited to, L cells L-M(TK$^-$) (ATCC CCL 1.3), L cells L-M (ATCC CCL 1.2), HEK293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), Xenopus melanophores, and Xenopus oocytes.

In a variation of the above-described cell-based assays, the present invention provides a method of high throughput screening to identify modulators of the activity of a receptor protein comprising:

(a) providing cells expressing said receptor proteins, said cells being present in virtual wells;

(b) exposing the cells to a substance suspected to be a modulator of the activity of said receptor protein;

(c) determining whether said substance modulates the activity of said receptor protein.

Microtiter-like plates containing virtual wells can be used in high throughput screening assays directed to the study of a number of biological processes, e.g., activity of ion channels, receptor binding, transcriptional or translational regulation or binding, reporter gene assays, assays for nuclear receptor binding or function, assays for protein translocation into or out of a cell or nucleus, enzymatic activity assays (protease, phosphatase, kinase, etc.).

The present invention provides a method of screening comprising:

(a) adding a series of reagents to a plurality of virtual wells in a microtiter-like plate;

(b) adding a spatially defined array of compounds to the plurality of virtual wells;

(c) incubating the reagents and compounds;

(d) reading a diagnostic signal from the virtual wells.

In particular embodiments, steps (a)–(c) are repeated, as many times as desired. In other embodiments, the total volume in the virtual wells after step (b) is about 100 nl to 10 $\mu$l.

If the reagents are added as a bulk fluid such as when plating cells, after washing, or when using a cheap reagent such as a stop reagent, and the plate or lid needs to be used at a later step in the assay as an array of fluid drops rather than as a bulk fluid tray, the bulk solution could be poured off and any remaining solution over the field could be removed by wicking it away with an absorbant material which is brought close to but not touching the surface so that the field become dry while the wells remain wet. The assay could then proceed as described above.

In the above-described method, the reagents and compounds can be added to the virtual wells by any of the methods discussed in this application, e.g., by a traditional pipetting or spotting method or by the aliquoting methods discussed in connection with virtual wells. If desired, the plate temperature during the reagent and compound dispensing step can be held to the dew point. The diagnostic signal can be read by any known detection method directly in the virtual wells. Alternatively, the top and bottom of the microtiter-like plate can be separated and one or more additional reagents can be added to the virtual wells before or during the reading of the plate, if necessary following an additional incubation.

The diagnostic signal can be any assayable variable commonly used in the art, for example: changes in membrane potential of cells; increases or decreases in metabolites or ions such as ATP, cAMP, cGMP, phospholipids, calcium, etc.; changes in the transcription of certain genes; changes in fluorescent or chemiluminescent behaviour; changes in pH; changes in enzymatic activity; cell growth or inhibition of growth; pigment dispersion or aggregation; antibody binding; etc.

Reagents can include any of the components that are normally used in screening assays, e.g., cells, buffers, enzymes, fluorescent or radioactive substances, antibodies, et c.

In particular embodiments of the above-described method, the microtiter-like plate has a top and a bottom, one or more of the components (i.e., reagents or compounds) is captured onto a solid surface for separation and washing prior to detection. Such embodiments comprise, after step (c) and before step (d), the additional steps of:

(i) separating the top and bottom of the microtiter-like plate and adding a new top that is engineered to bind one or more of the components in the virtual wells;

(ii) incubating as desired to allow binding of the component to the new top;

(iii) washing the bound component as desired;

(iv) repeating steps (i)–(iii) above as desired.

Figure 2B:
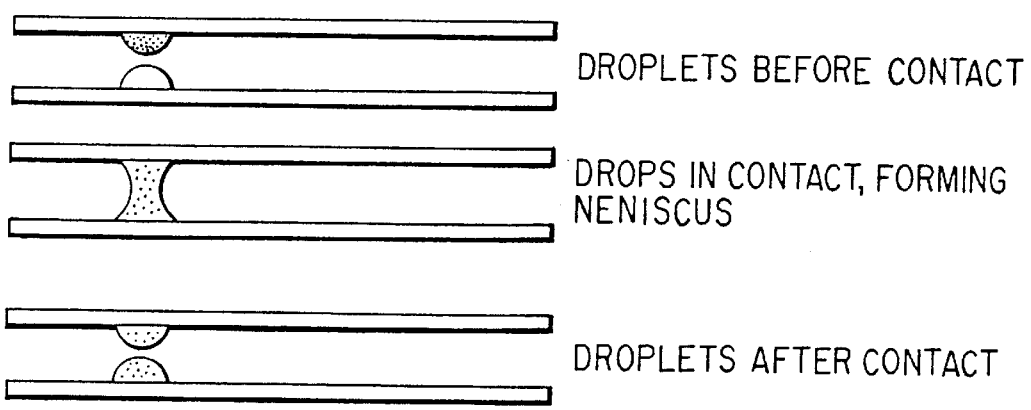
Figure 3A:
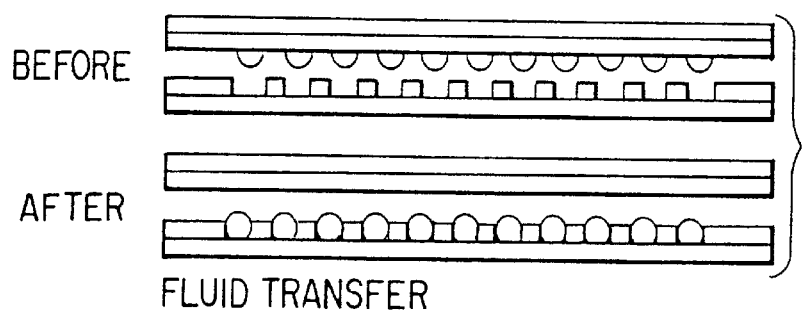
FIGS. 3A–C illustrates transfer, addition, and removal of fluid using plates containing virtual wells.
Figure 3B:
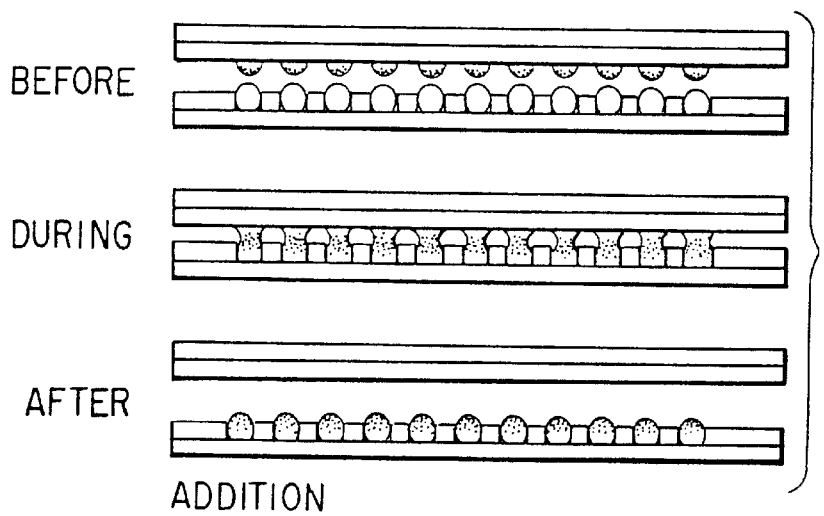
Figure 3C:
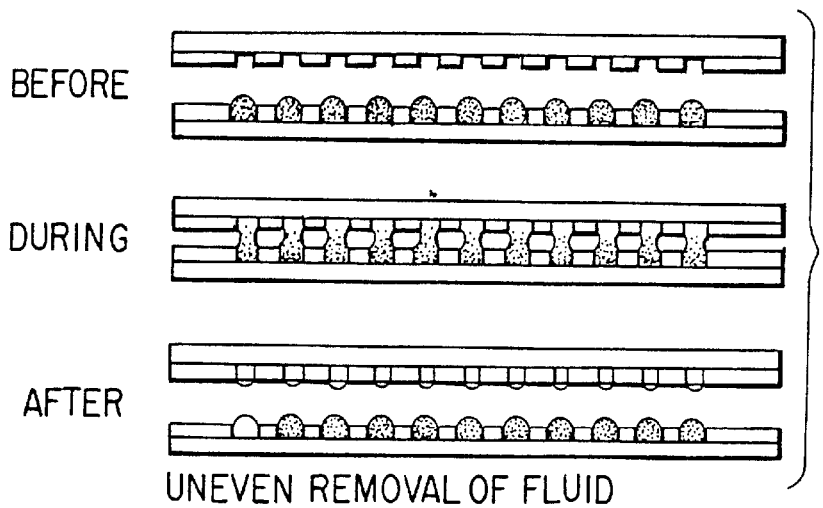
Figure 4A:
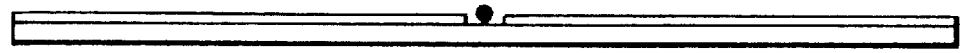
FIGS. 4A–E shows how the present invention can be used to repeatedly assay compounds from single combinatorial beads.
Figure 4B:
Figure 4C:
Figure 4D:
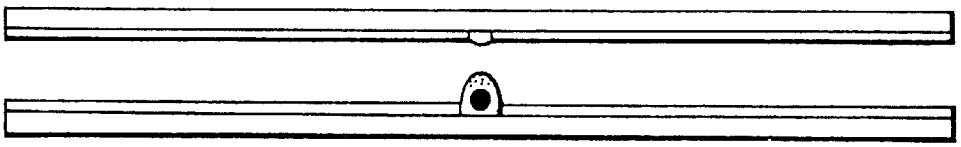
Figure 4E:
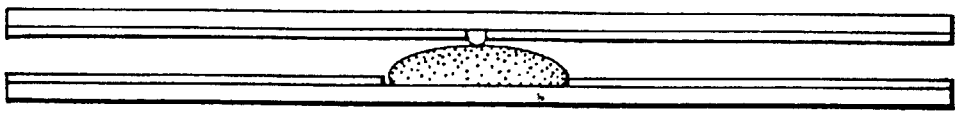
Figure 5A:
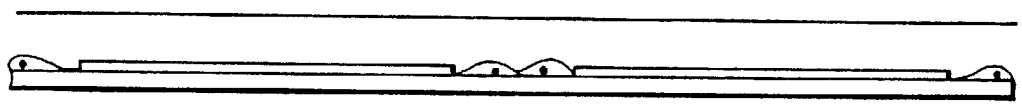
Figure 5B:
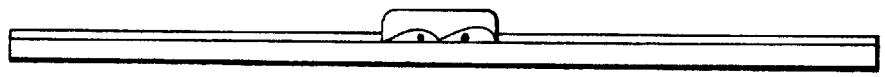
Figure 5C:
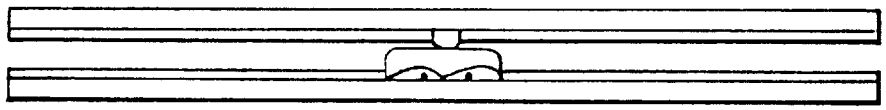
Figure 5D:
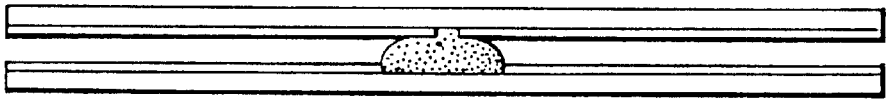
Figure 5E:
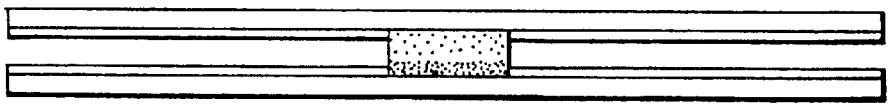

In contrast to current ultra high throughput screening systems, which are limited to running homogeneous fluorescent assays, screening systems that use plates containing virtual wells have numerous advantages. They are flexible, i.e., they can be used with a wide range of assay types, e.g., homogeneous assays, capture and wash assays, kinetic and flash detection assays. They are compatible with many detection methods such as: fluorescence, chemiluminescence (both glow and flash), absorbance, scattering, electroluminescence, isotope assays, as well as direct binding assays such as surface plasmon resonance (SPR), and reflective interference spectroscopy (RIfS). Plates containing virtual wells provide for consistent assay timing. Additions can be made to all the virtual wells on a plate simultaneously by moving two plates into close proximity (see, e.g., FIG. 2). Such simultaneous additions can be carried out while detection is occurring, e.g., for flash luminescence measurements. Simultaneous additions also allow the plates to be used for relatively fast kinetic assays. Virtual wells also have a clear, flat, reproducible optical path for improved reproducibility of optical measurements due to the lack of a meniscus.

The use of plates containing virtual wells provides an assay system where both the top and bottom of the plates are active components. By active components is meant, e.g., that either the top and bottom, or both, can be used for fluid transfer. Described herein are methods for fluid transfer using plates containing virtual wells. When an assay plate contains virtual wells in both its top and bottom, this increases the versatility of the assay compared to assays run in conventional plates in that fluid can be carried in the virtual wells of the top plate or the virtual wells of the bottom plate. Fluid can also be present in column-like virtual wells (see, e.g., FIG. 1), where the fluid touches the virtual wells of both the top and the bottom plates.

The present invention provides a method of adding fluid to a plurality of virtual wells comprising:

(a) providing a plate containing a plurality of virtual wells to which said fluid is to be added;

(b) moving said plate into close proximity to a fluid reservoir so that fluid is transferred from said reservoir to said plurality of virtual wells of said plate.

In particular embodiments, the fluid is transferred simultaneously to each of the plurality of virtual wells. In particular embodiments, step (b) involves dipping the plate into the reservoir and then shaking it dry. In a variation of the above-described method, rather than moving the plate into the reservoir, the plate is flooded and then shaken dry or blotted.

In all descriptions the plate and lid could be interchanged, since most of the fluid handling referred to here is largely if not completely independent of gravity (see Example 1).

One important advantage of virtual well plates is that they simplify the fluid handling, both pipetting and washing, necessary for running a broad variety of ultra high throughput assays. Virtual wells can be filled by most of the standard and not-so-standard pipetting devices used today, e.g., standard pipetting stations, semi- or fully-automated pipetting robots, or various inkjet type pipetting technologies, either directly into the wells or onto hydrophobic fields. Also, additions may be made by printing using pressure driven capillaries or passive pins or by spraying, flooding, or dipping the wells into a bulk solution.

In addition, virtual well plates can be filled by spotting fluid from one set of virtual wells to another, simply by moving the two plates into close proximity. This method of transfer is quite reproducible, typically involves much better than 10% variance, and is easy. It is particularly useful for replicating an array of different solutions multiple times, e.g., when one would like to run 10 or 100 or more assays on the same array of solutions. In this case, instead of having to pipette each of the solutions into each of the wells of each of the assays, all the solutions for a particular assay can be transferred in a single step. This process will save tremendous time and effort and allow one to avoid using many of the newest (and least optimized) pipetting systems.

During this spotting technique, the volume transferred will be largely but not entirely dependent on the relative ratios of the diameters of the two opposing virtual wells. Therefore, if one would like to transfer virtually all of the volume from a well, one can put the fluid to be transferred into small wells relative to the receiving wells. If one would like to transfer a smaller proportion of the fluid from a well, the fluid would be put into larger wells relative to the receiving wells.

Another method for transferring fluid would be to put the fluid to be transferred onto a relatively hydrophobic surface and then spot the fluid down on to either a dry or wet virtual well. The fluid will then leap from the relatively hydrophobic surface to the dry well or fluid in the well.

In addition to using the virtual wells for fluid addition and removal, they can be used for the easy removal of just one component or class of components by molecular capture. The capture could be done by gross physical properties such as charge attraction or by a very specific interaction such as with an antibody or nucleic acid or avidin-biotin type reaction. As an example, a kinase reaction could be run where a biotinylated peptide is used as the substrate and one measures the incorporation of $^{33}$P into the peptide from $^{33}$P-ATP. One way of running a typical protein kinase A screen would be to: dispense 500 nl of a mixture of the common reagents $^{33}$P-ATP, cold ATP, biotinylated peptide substrate, and reaction buffer to the bottom of a virtual well microtiter-like plate with well diameter of about 1.3 mm; pick up a plurality of 10 nl drops of compound by touching a lid array of 200–400 μm diameter wells to an array of compounds previously arrayed in 1–5 μl drops in about 1.3 mm i.d. wells; put the lid containing the compounds onto the bottom containing the previously dispensed reagents and incubate until mixed; dispense 500 nl of the enzyme in buffer to a second lid with virtual wells of diameter 200–900 μm; remove the lid (a 5–10 nl drop of the mixture will also be removed) containing the compounds and replace with the enzyme containing lid; incubate in the incubator for 30 minutes at 30° C.; remove the lid and replace with a streptavidin binding surface; incubate to capture the substrate; remove lid and wash by dunking it in various wash solutions, e.g., 1N NaCl, 1N NaCl with 1% $H_3PO_4$, $dH_2O$; and read the plate in a radioactive imager such as the InstantImager from Packard.

One of the advantages of the virtual well system is that both virtual wells and unpatterned binding surfaces can at one time hold assays that are spatially arrayed and be washed or have a bulk reagent added to them as if they were all one well. For instance, if a particular assay component is captured on a lid containing an array of virtual wells or a planar binding surface the lid could then be washed by dipping into a wash fluid, dipping into a circulating wash fluid, having a wash fluid streamed over the surface, or by blotting.

Since plates containing virtual wells are open only during the brief period while sample or reagents are being dispensed, there is little evaporation associated with their use. Evaporation can be further minimized by cooling plates to the dew point during dispensing. This method of controlling evaporation is advantageous compared to traditional methods such as increasing the humidity because it is less damaging to the instrumentation and stabilizes fragile reagents during the dispense.

The present invention provides a method of limiting evaporation during pipetting of assay reagents comprising:
(a) providing a microtiter plate containing multiple wells where said microtiter plate has been cooled to the dew point;
(b) pipetting assay reagents into said wells of said microtiter plate while the temperature of said microtiter plate is kept at or near the dew point.

The above-described method can be incorporated into various high throughput screening systems in order to provide for less variability between results since the volumes assayed in each well will vary less due to less evaporation occurring. In order to keep the temperature of the plate at the dew point, one can employ a sensor based on resistivity or use more traditional means such as measuring temperature and relative humidity.

The present invention provides a method of simultaneously adding fluid to a plurality of virtual wells comprising:
(a) providing a first plate containing a plurality of virtual wells to which said fluid is to be added;
(b) providing a second plate on which said fluid is present;
(c) moving said second plate into close proximity to said first plate so that fluid is transferred from said second plate simultaneously or near simultaneously to said plurality of virtual wells of said first plate.

In a particular embodiment, the second plate also contains virtual wells and the fluid is transferred from the virtual wells of the second plate to the virtual wells of the first plate.

In a particular embodiment, a known, preselected volume of fluid is added to each virtual well of the first plate. This can be accomplished by utilizing a second plate that also contains virtual wells and by choosing the relative sizes and hydrophilicities of the virtual wells of the first and second plates appropriately, so that addition of the preselected volume occurs.

In a particular embodiment, the method further comprises determining whether a preselected biological activity is present in the virtual wells of the first plate while fluid is transferred from the second plate to the virtual wells of the first plate.

In the above-described method, and in similar methods of transferring fluid between two plates, one of skill in the art would understand that, in order to effect simultaneous transfer of fluid to the plurality of virtual wells of the first plate, the first plate and the second plate should be parallel during the transfer.

The present invention provides a method of simultaneously removing fluid from a plurality of virtual wells comprising:
(a) providing a first plate containing a plurality of virtual wells in which said fluid is present;
(b) providing a second plate onto which said fluid is to be transferred;
(c) moving said second plate into close proximity to said first plate so that fluid is transferred simultaneously from said plurality of virtual wells of said first plate to said second plate, thus removing said fluid from said virtual wells of said first plate.

In a particular embodiment, a known, preselected volume of fluid is removed from each virtual well of the first plate. This can be accomplished by utilizing a second plate that also contains virtual wells and by choosing the relative sizes and hydrophilicities of the virtual wells of the first and second plates appropriately, so that transfer of the preselected volume occurs.

If the preselected volume transferred to the second plate is small relative to the volume present in each virtual well of the first plate, the method can be practiced multiple times with the same first plate, thereby providing a way of transferring the same volume of fluid multiple times from a single plate. If the plurality of virtual wells in the first plate represents an array of different solutions, i.e., a different solution in each virtual well, with the identity of each solution (although not necessarily the nature of its chemical contents) and its position in the array of virtual wells being known, then the above-described method permits one to recreate that array multiple times, on multiple other plates. An example of when such a method would be especially valuable would be if one had an array composed of a plurality of solutions, each solution containing a different compound from a combinatorial library, and each solution being present in a different virtual well. In a variation of the above-described method, rather than transferring the same volume from the virtual wells of the first plate multiple times, a different volume is transferred each time. This can be easily accomplished by using a second plate that also contains virtual wells and by varying the size arid hydrophilicity of the virtual wells of the second plate.

A variation of the present invention makes use of "reverse virtual wells." Such reverse virtual wells are made by arranging hydrophobic domains within hydrophilic fields. Reverse virtual wells are used to confine hydrophobic assay mixtures, e.g., assay mixtures made up of organic solvents or synthetic chemistry reactions. Plates containing reverse virtual wells similar to those containing virtual wells described above are provided by the present invention. Plates containing reverse virtual wells can be made and used in a manner similar to that described above for virtual wells.

Accordingly, the present invention provides a novel microtiter-like plate comprising:

(a) a bottom having an upper surface comprising a plurality of reverse virtual wells, said reverse virtual wells being hydrophobic domains within a hydrophilic field, and a continuous upstanding sidewall or spacer along the perimeter of the bottom;

(b) a cover configured for enclosing said bottom by resting on said sidewall or spacer.

The present invention also provides a novel microtiter-like plate comprising:

(a) a bottom having an upper surface comprising a plurality of reverse virtual wells, said reverse virtual wells being hydrophobic domains within a hydrophilic field, and a continuous upstanding sidewall or spacer along the perimeter of the bottom;

(b) a top having a lower surface comprising a plurality of reverse virtual wells or a solid hydrophilic surface, said top configured for enclosing said bottom by resting on said sidewall or spacer;

wherein said plurality of reverse virtual wells of said bottom and said plurality of reverse virtual wells of said top are present in an arrangement such that when said bottom and said top are in close proximity column-like reverse virtual wells are formed between said bottom and said top.

In addition to the microtiter-like plates containing virtual wells described above, the present invention also provides an inexpensive, disposable device for transferring small volumes of a spatial array of fluids from a first microtiter plate to a second microtiter plate, preserving the spatial array in the process. Each element in the spatial array can be a different fluid, either due to the nature of the liquid part of the fluid or due to the nature of compounds dissolved in the liquid, or both. The first microtiter plate can be a storage plate, having a large volume of the fluids relative to the volume transferred. Alternatively, the device of the present invention can be used to transfer fluid from a tray containing a homogeneous fluid rather than from a first microtiter plate containing a spatial array of fluids. In such use, the device transfers multiple constant amounts of the fluid in a spatial array to a microtiter plate where each element in the spatial array is the same fluid.

The device of the present invention is essentially a series of pins or passive transfer elements that work in a somewhat similar fashion to the Biomek 2000 HDR tool or manual pin replication tools. One major difference between the present invention and the prior art is that the device is manufactured so that it can reproducibly transfer volumes in the low nanoliter range, 100 nl to 100 pl. This is accomplished by using a micromachining technique such as, for example: anisotropic, isotropic, plasma, or reactive ion etching or similar technique originally designed for the manufacture of integrated circuits (see Silicon Chemical Etching, Freyhardt, H. C. editor, New York:Springer-Verlag-New-York-Inc., December 1982, or Plasma Etching: An Introduction, Manos, Dennis M.; Flamm, Daniel L., Academic Press Inc., July 1989 for general descriptions of these types of processes); machining by wire EDM (electron discharge machining) (see The EDM Handbook, Guitrau, E. P., Cincinnati: Hanser-Gardner-Pub., October 1997); laser cutting with or without a subsequent etching step to improve the surface finish; or molding by an injection or thermoforming process. For instance, three reasonable methods for making the device would be to anisotropically wet etch a 111 silicon wafer to obtain near vertical square posts, isotropically wet etch glass with KOH or similar etchant for round tapered posts, or use wire EDM to machine a steel or alloy block into an array of square posts. Due to cost, achievable tolerances, and surface finish considerations, anisotropic or isotropic wet etching and EDM manufacturing appear preferable. Another difference from prior art is that the device can be specifically designed to act as a lid for storage of a spatial array of chemicals or solutions and this lid feature allows the device and the array to automatically align.

Unlike other prior art devices, the devices of the present invention are generally made by the use of relatively inexpensive machining or micromachining processes. This allows for the devices of the present invention to be relatively disposable. While the devices of the present invention are generally disposable, there is no reason why one could not re-use them if one so chose. One situation where the devices might be re-used without risking contamination is where the devices are used not only to transfer fluids but also as lids for storage plates. Here, because of their one to one correspondance to a spatial array of solutions the same pin will always see the same solution so there is no risk of cross contamination. Of course, re-using the devices for multiple arrays of solutions entails giving up certain of the advantages provided by the devices. For example, one would then have to wash the pins of the devices between uses.

The prior art contains devices such as the replicator made by V&P Scientific, Inc. (1997, J. Biomolec. Screen. 2: 118) or the HDR pin tool on the Biomek 2000 from Beckman, Inc. have flat or grooved pins where fluid is transferred by virtue of being trapped by surface tension or capillary action in the grooves of the pins. The pin array is then removed, washed, and reused with new compounds. Unlike such prior art devices, the devices of the present invention are part of a microtiter like plate. This difference allows them to be self aligning, to act as evaporation barriers for compound stores, and to prevent any risk of cross contamination of compounds from one array to another. This difference also speeds up the execution of the assays because washing is no longer required. Another difference is that the faces of the device of the present invention can be made from hydrophilic or hydrophobic material, or can be coated with a hydrophilic or hydrophobic material, depending on the nature of the fluids it is desired to transfer on the faces. One method for doing so would be to coat the tip of the pins with photoresist or other resist and then pour, dip or spray a diluted wax or other hydrophobic coating onto the entire part prior to removing the resist.

The present invention provides a device for transferring fluids where the device has a plurality of pins that have been micromachined into the surface of a material such as glass, silicon or other crystalline material by a process selected from the group consisting of anisotropic, isotropic, plasma, or reactive ion etching and where the pins have a circular, square, or other closed polygon face having a diameter of from 50 $\mu$m to 1 mm and the pins have a depth of 0.3 to 10 mm and where the device transfers a volume of fluid between 100 pl and 1 $\mu$l. Alternatively, the device could be electron discharge machined from metal or other conductive material; laser cut from any of the preceeding materials or a plastic; or molded from a plastic or glass or metal.

In particular embodiments, the diameter of the faces of the pins is between 200–400 µm.

The device of the present invention is especially useful in high throughput screening. In such use, the device would be used as a transfer tool for removing about 10 nl volumes (although it could be made to deliver other volumes, e.g., 2–5,000 nl; 10–2,000 nl; 50–1,000 nl, etc.) from a storage plate and spotting those volumes onto an assay plate. The device could then be returned to the storage plate to act as a lid for storage.

The device of the present invention can be manufactured from a variety of materials. One possibility is to make the device by micromachining glass. However, the device could be made from any etchable material with or without a coating such as gold. Examples of such etchable materials are: glass, metals, silicon or other crystaline material, plastics, and ceramics.

The device of the present invention can be used to transfer fluids to a variety of types of plates. One preferred use is to use the device to transfer fluid to and from microtiter-like plates containing virtual wells. The use of the device of the present invention to transfer fluid to and from microtiter-like plates containing virtual wells can simplify the use of these plates and magnify their many advantages as compared to conventional microtiter plates.

The present invention provides a combination of a device and a microtiter-like plate where the device acts as a lid for the microtiter-like plate and where the device has a plurality of pins where the pins have been produced by a process selected from the group consisting of:

micromachining into the surface of a material selected from the group consisting of glass, silicon and other crystalline materials by a process selected from the group consisting of anisotropic, isotropic, plasma, and reactive ion etching;

electron discharge machining into the surface of a material selected from the group consisting of metal and other conductive materials;

laser cutting into the surface of a material selected from the group consisting of glass, silicon or other crystalline material; metal or other conductive materials; and plastic;

molding from a material selected from the group consisting of plastic, glass, and metal;

where the pins have a circular or other closed polygon face having a diameter of from 50 to 700 µm;

where the pins have a depth of 0.3 to 10 mm; and where the device transfers a volume of fluid between 100 pl and 100 nl.

In particular embodiments of the combination, the microtiter-like plate contains virtual wells.

The present invention provides methods of transferring fluid to and from a microtiter plate by the use of the device of the present invention.

The present invention provides a method of transferring fluid from a first microtiter plate to a second microtiter plate that comprises:

(a) providing a plurality of fluids present in a spatial array in the wells of a first microtiter plate;

(b) providing a device having pins arranged in a spatial array similar to the spatial array of the wells in the first microtiter plate;

(c) moving the device into close proximity to the first microtiter plate so that the spatial array of pins in the device matches the spatial array of wells of the first microtiter plate so that fluid is transferred from the wells of the first microtiter plate to the pins of the device;

(d) moving the device into close proximity to a second microtiter plate having wells arranged in a spatial array similar to the spatial array of the first microtiter plate and to the the spatial array of the pins of the device so that fluid is transferred from the pins of the device to the wells of the second microtiter plate;

where the spatial array of the fluid in the first microtiter plates is transferred to the second microtiter plate;

where the device has a plurality of pins where the pins have been produced by a process selected from the group consisting of:

micromachining into the surface of a material selected from the group consisting of glass, silicon and other crystalline materials by a process selected from the group consisting of anisotropic, isotropic, plasma, and reactive ion etching;

electron discharge machining into the surface of a material selected from the group consisting of metal and other conductive materials;

laser cutting into the surface of a material selected from the group consisting of glass, silicon or other crystalline material; metal or other conductive materials; and plastic;

molding from a material selected from the group consisting of plastic, glass, and metal;

where the pins have a circular or other closed polygon face having a diameter of from 50 to 700 µm;

where the pins have a depth of 0.3 to 10 mm; and where the device transfers a volume of fluid between 100 pl and 100 nl.

The present invention provides a method of removing fluid from a plurality of wells in a spatial array comprising:

(a) providing a microtiter-like plate containing a plurality of wells in a spatial array in which fluid is present;

(b) moving a device having pins in a spatial array similar to the spatial array of the wells of the microtiter-like plate into close proximity to the microtiter-like plate so that fluid is transferred from the wells of the microtiter-like plate to the pins of the device, the fluid from each well of the microtiter-like plate being transferred to a single pin, and where the spatial array of fluids in the wells of the microtiter-like plate is preserved on the pins;

where the device has a plurality of pins where the pins have been produced by a process selected from the group consisting of:

micromachining into the surface of a material selected from the group consisting of glass, silicon and other crystalline materials by a process selected from the group consisting of anisotropic, isotropic, plasma, and reactive ion etching;

electron discharge machining into the surface of a material selected from the group consisting of metal and other conductive materials;

laser cutting into the surface of a material selected from the group consisting of glass, silicon or other crystalline material; metal or other conductive materials; and plastic;

molding from a material selected from the group consisting of plastic, glass, and metal;

where the pins have a circular or other closed polygon face having a diameter of from 50 to 700 µm;

where the pins have a depth of 0.3 to 10 mm; and where the device transfers a volume of fluid between 100 pl and 100 nl.

If the volume removed from the wells of the microtiter-like plate is small relative to the volume present in the wells of the microtiter-like plate, the method can be practiced multiple times with the same microtiter-like plate, thereby providing a way of transferring the same volume of the same spatial array of fluid multiple times from a single microtiter-like plate. If the plurality of wells in the microtiter-like plate represents an array of different solutions, i.e., a different solution in each well, with the identity of each solution (although not necessarily the nature of its chemical contents) and its position in the array of wells being known, then the above-described method permits one to recreate that array multiple times, on multiple other microtiter-like plates. An example of when such a method would be especially valuable would be if one had an array composed of a plurality of solutions, each solution containing a different compound from a combinatorial or chemical library, and each solution being present in a different well. In a variation of the above-described method, rather than transferring the same volume from the wells of the microtiter-like plate multiple times, a different volume is transferred each time. This can be easily accomplished by using devices having pins of varying face size or hydrophilicity.

The present invention provides a method of adding fluid to a plurality of wells in a microtiter plate in a spatial array comprising:

(a) providing a microtiter plate containing a plurality of wells in a spatial array into which the fluid is to be added;

(b) moving a device having pins coated with fluid where the pins are arranged in a spatial array similar to the spatial array of the wells of the microtiter plate into close proximity to the microtiter plate so that fluid is transferred from the pins to the wells of the microtiter plate, the fluid from each pins being transferred to a single well and where the spatial array of fluids on the pins is preserved in the wells;

where the device has a plurality of pins where the pins have been produced by a process selected from the group consisting of:

micromachining into the surface of a material selected from the group consisting of glass, silicon and other crystalline materials by a process selected from the group consisting of anisotropic, isotropic, plasma, and reactive ion etching;

electron discharge machining into the surface of a material selected from the group consisting of metal and other conductive materials;

laser cutting into the surface of a material selected from the group consisting of glass, silicon or other crystalline material; metal or other conductive materials; and plastic;

molding from a material selected from the group consisting of plastic, glass, and metal;

where the pins have a circular or other closed polygon face having a diameter of from 50 to 700 $\mu$m;

where the pins have a depth of 0.3 to 10 mm; and where the device transfers a volume of fluid between 100 pl and 100 nl.

In particular embodiments of the above-described methods, the fluids contain dissolved compounds in DMSO. In other embodiments, the fluids are $H_2O$, DMSO, DMSO mixed with a second solvent such as water or MeOH or other common solvents. Whatever the fluid, the fluid may contain dissolved compounds.

In a particular embodiment of the above-described methods, the method further comprises determining whether a preselected biological activity is present in the wells of a microtiter plate after fluid is transferred from the pins into the wells of the microtiter plate.

In the above-described methods, and in similar methods of transferring fluid, one of skill in the art would understand that, in order to effect simultaneous transfer of fluid to or from the plurality of wells of the microtiter plates, the microtiter plates and the faces of the pins of the device should be parallel during the transfer. One of skill in the art would also understand that, in order for the pins of the device to align properly with the wells of the microtiter plate, the device and plate can be particularly designed for such purpose, as, e.g., by having posts in the plate into which apertures in the device fit, or by other methods of configuring the device and the plate so that it fits as a lid on the plate in only a single orientation. Such designs ensure that the spatial array of the wells of the plate is recreated on the pins, or vice versa. One of skill in the art would also understand that the device can act as an evaporation control barrier for the plate.

In particular embodiments of the above-described methods, the wells of the first microtiter plate are virtual wells. In other embodiments, the wells of the second microtiter plate are virtual wells. In other embodiments, the wells of both the first and the second microtiter plate are virtual wells. In a particular embodiment, a known, preselected volume of fluid is removed from or added to each virtual well of a microtiter plate. This can be accomplished by utilizing a device containing pins of a preselcted face size and made of a material having a preselected hydrophilicity relative to the hydrophilicity of the material making up the virtual wells of the microtiter plate.

In particular embodiments of the above-described methods, the pins of the device have circular or closed polygons such as square faces with diameters of about 300 $\mu$m but alternatively between 50 and 700 $\mu$m and transfer volumes of about 10 nl but alternatively between 100 pl and 100 nl.

The preferred method for making the devices appears to be wet etching of glass or silicon or EDM machining of metal, particularly corrosion resistant steels, other alloys such as Monel and Zircalloy, or nobel metals such as gold, platinum or titanium. Secondary methods would be dry etching, such as plasma or reactive ion etching of glass, silicon, or other crystalline material, laser milling of any of the above materials, or molding (injection or otherwise) of plastics.

The following non-limiting examples are presented to better illustrate the invention.

EXAMPLE 1

Transfer of Liquid from one Patterned Glass Slide Containing Virtual Wells to Another by Moving the two Slides into and out of Close Proximity Glass slides were patterned by printing the desired pattern as drawn in an autocad file onto transparency film using a wax transfer laser jet system from Tektronic and then gluing the transparency to the glass slide. The diameter of the virtual wells formed was about 1.524 mm. 2.5 $\mu$l of dilute fluorescein solution was added to each virtual well on the bottom slide by hand pipetting. A 815 $\mu$m tall spacer was taped across both ends of the bottom slide and the top slide was placed on top of the spacers so that the top and bottom slides were in close opposition, with the drops of fluorescein solution in the virtual wells of the bottom slide being in contact with the virtual wells of the top slide. The top slide was then removed, with some of the solution from the bottom slide being carried off in the virtual wells of the top slide. In order to measure the amount of fluorescein (and thus the amount of solution transferred), 350 μm tall spacers were added to the top slide and another, third plain slide placed on these spacers. The amount of fluorescein in the virtual wells of the top and third slides was measured in a Fluorimager (Molecular Dynamics). The results are shown in Table 1.

TABLE 1

|  | t | s | u | q | p | r |
|---|---|---|---|---|---|---|
| volume, μl | 2.5 | 2.5 | 2.5 | 2.5 | 2.5 | 2.5 |
| fluorescein conc. | 0.0005 | 0.0005 | 0.001 | 0.001 | 0.001 | 0.0001 |
| n | 10 | 4 | 6 | 10 | 10 | 10 |
| avg | 57440 | 64605 | 124973 | 126558 | 136759 | 6463 |
| sd | 4325 | 3046 | 4888 | 12086 | 11654 | 678 |
| cv | 8% | 5% | 4% | 10% | 9% | 10% |
| removed from | top | bottom | bottom | top | top |  |

In Table 1, t, s, u, q, p, and r represent separate sets of experiments. In p, q, s, t, and u, the fluid was removed by moving the top slide into close proximity to the bottom slide. In r, the fluid was removed and transferred into the virtual wells of the top slide by hand pipetting. In s and u, before the top and bottom slides were moved out of close proximity, the orientation of the slides was reversed, so that the bottom slide was now the upper slide while the top slide was the lower slide. In p, q, and t, the top slide was simply removed upward, without first reversing the orientation of the slides.

In the rows of Table 1, "n" represents the number of times a particular set of experiments was repeated. "avg" represents the average fluorescence measurement from the virtual wells for a particular set of experiments, i.e., the amount of solution transferred. "sd" represents the standard deviation of that average. "cv" represents the coefficient of variance for a particular set of experiments.

The results shown in Table 1 demonstrate that fluid can be transferred from the virtual wells of one slide to the virtual wells of another slide in such a way that the variance in amount transferred is less than 10%. This is less variance than the variance observed when the fluid was transferred by hand (i.e., not using virtual wells). The variance when using transfer by hand was 10% (see row r of Table 1.)

As a further test of the ability of virtual wells to transfer fluid in reproducible amounts from slide to slide, virtual wells on a first slide were filled with 5 μl of 1N HCl. The slides used were commercially available TEFLON® coated glass slides (Erie Scientific, Portsmouth, N.H.). The TEFLON® is patterned so as to leave areas of glass exposed having a diameter of 2 mm. A 1.27 mm spacer was added and a second slide, also containing virtual wells, was moved into close proximity to the first slide, thus transferring a portion of the fluid from the virtual wells of the first slide to the virtual wells of the second slide. The second slide was then placed on top of a third slide that contained a known volume of 0.8N NaOH with a pH sensitive dye (bromoxynol blue). Thus, the color of the dye was determined by the final pH of the mixture formed by the transfer of 1N HCl solution to 0.8 N NaOH solution. This final pH depends on the amount of 1N HCl solution transferred as well as on the amount of 0.8N NaOH solution in the virtual wells of the third slide. If the amount of 1N HCl solution transferred is more or less constant, then the final pH (and the color of the dye) will appear to depend only on the amount of 0.8N NaOH solution in the virtual wells of the third slide. Table 2 shows that this is what was experimentally observed.

TABLE 2

| Volume of 0.8N NaOH per well of third slide | Percent blue wells | Percent yellow wells |
|---|---|---|
| 2.2 μl | 100 | 0 |
| 2.1 μl | 50 | 50 |
| 2.0 μl | 9 | 91 |
| 1.9 μl | 14 | 86 |

An experiment similar to that described above was done using transfer of $H_2O$ containing $^{33}P$-labeled ATP from one slide to another. In this case, a spacer was not used. The results were essentially the same although the variance was slightly higher.

Protein solutions of 0.1%, 1%, 5%, and 10% bovine serum albumin (BSA) were reproducibly transferred from one slide containing virtual wells to another. 3 μl of the BSA solutions were pipetted into 2 mm virtual wells contained on commercially available TEFLON® coated glass slides (Cell Line). The TEFLON® was patterned so as to leave areas of glass exposed having a diameter of 2 mm. The BSA solutions were transferred to a second slide by the use of a 40 mil spacer. The percent of solution transferred was found to be independent of BSA concentration and to be highly reproducible; the variances in amount transferred were much less than 10%. In general, about 40–45% of the BSA solutions were transferred to the second slide.

EXAMPLE 2

Transfer of Fluid Multiple Times from Virtual Wells

5 μl of $^{33}P$-labeled $H_2O$ containing Malachite Green (to make it easier to see the $H_2O$) was added to virtual wells on a glass slide. The slides used were commercially available TEFLON® coated glass slides (Cell Line). The TEFLON® was patterned so as to leave areas of glass exposed having a diameter of 2 mm. Fluid was transferred from the wells of this slide five successive times to five other slides by moving the other slides into close proximity to the first slide. The first transfer was done without a spacer; the next four transfers were done with a 40 mil spacer. The slides were dried, wrapped in plastic wrap, and measured on an InstantImager from Packard. The transfer variance on any given slide was between 4% and 10% and the variance across all five slides was 10%.

The above-described experiment was repeated with DMSO rather than $H_2O$ as the solvent and with the virtual wells in the top slides (to which the DMSO was transferred) having a diameter of 1 mm rather than 2 mm. The transferred volume was 400 nl per well and the variance was 20%. This type of experiment was repeated multiple times; the variances observed ranged from 3% to 14%. Some of the experiments were done with a series of gradually thinner spacers, from 50 mil to 20 mil. There was no correlation between spacer thickness and amount transferred.

EXAMPLE 3

Cooling Slides to the Dew Point Limits Evaporation

The evaporation of a drop of water (approximately 20 nl to 30 nl) as a function of room temperature, room humidity, and the surface temperature of the slide on which the drop is placed was studied. 30 drops were dispensed simultaneously by piezo pipetting tip onto the surface of a glass slide and the time until the last drop evaporated was monitored. The results are shown in Table 3.

TABLE 3

| % RH | bench temp | plate temp | time to evap. |
|---|---|---|---|
| 38 | 72 | 22 | 55 |
| 37 | 72 | 17.1 | 99 |
| 37 | 72 | 17.6 | 88 |
| 37 | 72 | 17.7 | 72 |
| 37 | 72 | 14.2 | 141 |
| 37 | 72 | 13.7 | 154 |
| 36 | 72 | 13.6 | 155 |
| 36 | 72 | 12.5 | 187 |

TABLE 3-continued

| % RH | bench temp | plate temp | time to evap. |
|---|---|---|---|
| 36 | 72 | 10.6 | 281 |
| 36 | 72 | 9.9 | 344 |
| 36 | 72 | 9.8 | 342 |
| 36 | 72 | 8 | 820 |
| 36 | 73 | 8 | 991 |
| 36 | 74 | 8.1 | 1179 |
| 36 | 74 | 7.3 | 2100 |
| 36 | 74 | 8.1 | >3600 |
| 36 | 74 | 8.1 | 222 |
| 35 | 75 | 8.1 | 353 |
| 35 | 75 | 8.1 | 481 |

It can be seen from Table 3 that cooling the surface of the slide resulted in substantially increasing the time until the last drop evaporated. Of course, the surface of the slide cannot be cooled indefinitely; at some point condensation will occur. The aim is to cool the surface until just before this happens. The temperature up until which one can cool the surface and yet not have condensation occur can be easily calculated.

One could do this, for example, by constructing a table such as Table 4. Across the top row of Table 4 is the room temperature in degrees Fahrenheit. Down the first column is the plate temperature in degrees Celsius. Down the second column is the corresponding maximum number of grams of water that 1 cubic meter of air can hold at 1 atmosphere pressure as given in chart E-37 in the CRC Handbook of Chemistry and Physics, 69th edition, which lists saturation volumes of water in air as a function of temperature. The rest of the columns list the relative humidity that corresponds to any given plate temperature as a function of room temperature. Therefore, if one knows the room temperature and relative humidity, one can find that entry in the table corresponding to that combination of room temperature and relative humidity and look across to the first column on the left to see the temperature at which the plate should be kept at so that the plate is at the dew point.

TABLE 4

| temp | CRC E-37 mass H2O (g)m3 | % 84.2 F % of 29 | % 84.4 F % of 28 | % 80.6 F % of 27 | % 78.8 F % of 26 | % 77 F % of 25 | % 75.2 F % of 24 | % 73.4 F % of 23 | % 71.6 F % of 22 | % 68.8 F % of 21 | % 67 F % of 20 |
|---|---|---|---|---|---|---|---|---|---|---|---|
| 0 | 4.847 | 17% | 18% | 19% | 20% | 21% | 22% | 24% | 25% | 26% | 28% |
| 1 | 5.129 | 18% | 19% | 20% | 21% | 22% | 24% | 25% | 26% | 28% | 30% |
| 2 | 5.559 | 19% | 20% | 22% | 23% | 24% | 26% | 27% | 29% | 30% | 32% |
| 3 | 5.947 | 21% | 22% | 23% | 24% | 26% | 27% | 29% | 31% | 32% | 34% |
| 4 | 6.36 | 22% | 23% | 25% | 26% | 28% | 29% | 31% | 33% | 35% | 37% |
| 5 | 6.797 | 24% | 25% | 26% | 28% | 29% | 31% | 33% | 35% | 37% | 39% |
| 6 | 7.26 | 25% | 27% | 28% | 30% | 31% | 33% | 35% | 37% | 40% | 42% |
| 7 | 7.75 | 27% | 28% | 30% | 32% | 34% | 36% | 38% | 40% | 42% | 45% |
| 8 | 8.27 | 29% | 30% | 32% | 34% | 36% | 38% | 40% | 43% | 45% | 48% |
| 9 | 8.819 | 31% | 32% | 34% | 36% | 38% | 40% | 43% | 45% | 48% | 51% |
| 10 | 9.399 | 33% | 35% | 36% | 39% | 41% | 43% | 46% | 48% | 51% | 54% |
| 11 | 10.01 | 35% | 37% | 39% | 41% | 43% | 46% | 49% | 52% | 55% | 58% |
| 12 | 10.66 | 37% | 39% | 41% | 44% | 46% | 49% | 52% | 55% | 58% | 62% |
| 13 | 11.35 | 39% | 42% | 44% | 47% | 49% | 52% | 55% | 58% | 62% | 66% |
| 14 | 12.07 | 42% | 44% | 47% | 50% | 52% | 55% | 59% | 62% | 66% | 70% |
| 15 | 12.83 | 45% | 47% | 50% | 53% | 56% | 59% | 62% | 66% | 70% | 74% |
| 16 | 13.63 | 47% | 50% | 53% | 56% | 59% | 63% | 66% | 70% | 74% | 79% |
| 17 | 14.48 | 50% | 53% | 56% | 59% | 63% | 66% | 70% | 75% | 79% | 84% |
| 18 | 15.37 | 53% | 56% | 60% | 63% | 67% | 71% | 75% | 79% | 84% | 89% |
| 19 | 16.31 | 57% | 60% | 63% | 67% | 71% | 75% | 79% | 84% | 89% | 94% |
| 20 | 17.3 | 60% | 64% | 67% | 71% | 75% | 79% | 84% | 89% | 94% | 100% |
| 21 | 18.34 | 64% | 67% | 71% | 75% | 80% | 84% | 89% | 94% | 100% | |
| 22 | 19.43 | 68% | 71% | 75% | 80% | 84% | 89% | 94% | 100% | | |

TABLE 4-continued

| temp | CRC E-37 mass H2O (g)m3 | % 84.2 F % of 29 | % 84.4 F % of 28 | % 80.6 F % of 27 | % 78.8 F % of 26 | % 77 F % of 25 | % 75.2 F % of 24 | % 73.4 F % of 23 | % 71.6 F % of 22 | % 68.8 F % of 21 | % 67 F % of 20 |
|---|---|---|---|---|---|---|---|---|---|---|---|
| 23 | 20.58 | 72% | 76% | 80% | 84% | 89% | 94% | 100% | | | |
| 24 | 21.78 | 76% | 80% | 84% | 89% | 94% | 100% | | | | |
| 25 | 23.05 | 80% | 85% | 89% | 95% | 100% | | | | | |
| 26 | 24.38 | 85% | 90% | 95% | 100% | | | | | | |
| 27 | 25.78 | 90% | 95% | 100% | | | | | | | |
| 28 | 27.24 | 95% | 100% | | | | | | | | |
| 29 | 28.78 | 100% | | | | | | | | | |
| 30 | 32.38 | | | | | | | | | | |

Figure 7A:
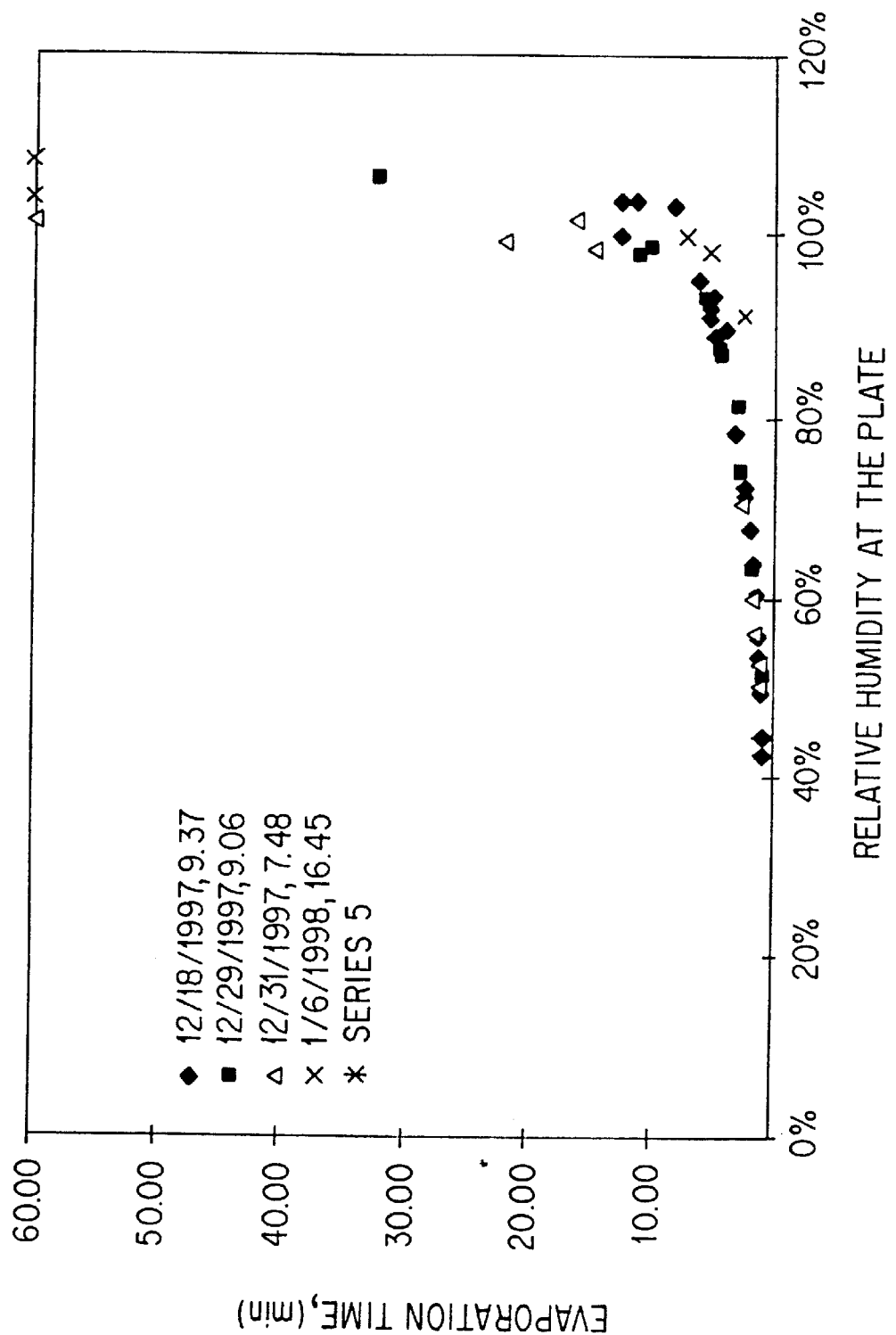
FIGS. 7A–B shows the evaporation of a drop of water from the surface of a glass slide as a function of water saturation at the surface of the glass slide.
Figure 7B:
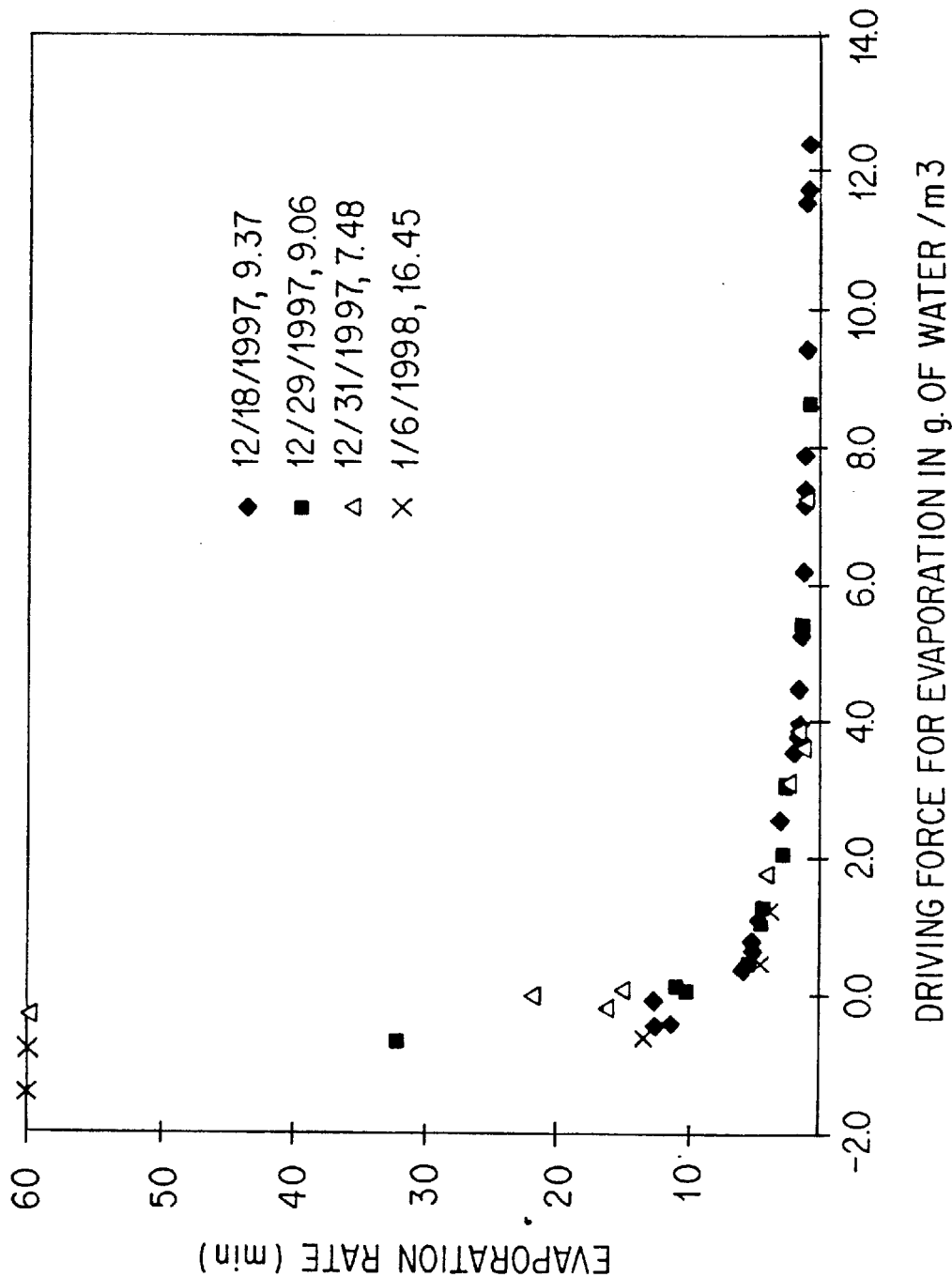
Figure 8A:
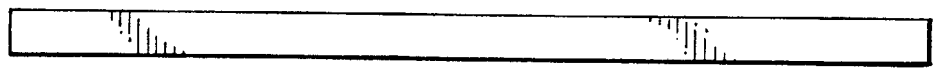
FIG. 8A depicts the starting material. The starting material can be any etchable, machinable or moldable material, e.g., glass, silicon, metal, ceramics, plastics, or crystals.
Figure 8B:
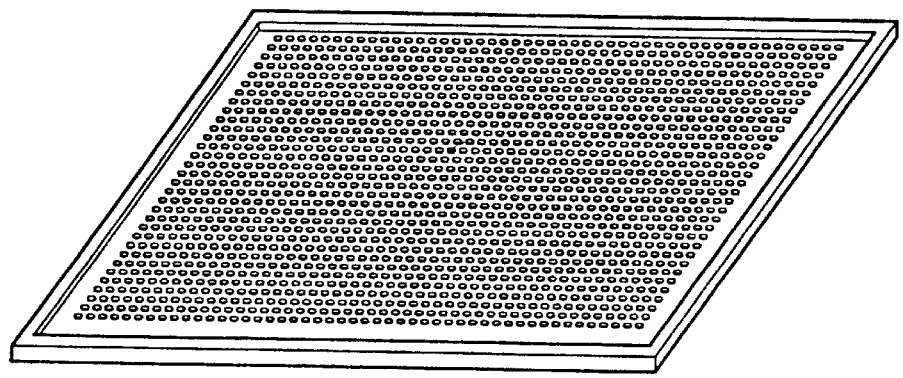
FIG. 8B depicts the starting material after a mask pattern has been transferred to it by photolithography.
Figure 8C:
FIG. 8C depicts a small portion of the device after it has been etched to create stubs or pins.
Figure 8D:
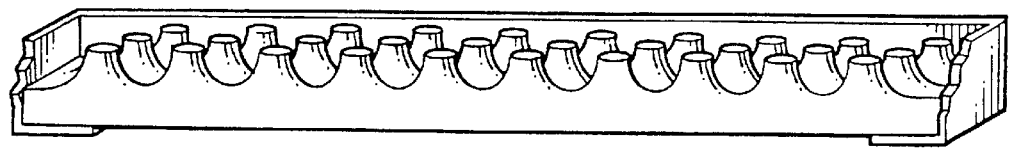
FIG. 8D depicts the device assembled into one half of a microtiter-like plate.
Figure 9A:
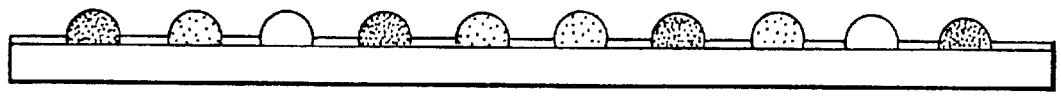
FIG. 9A depicts a storage plate, from which fluid is to be transferred by the device. In this case, the storage plate is a plate containing virtual wells, but the storage plate can also be a conventional microtiter plate or a tray containing a single solution.
Figure 9B:
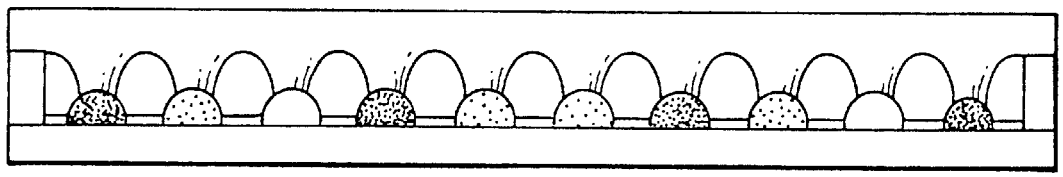
FIG. 9B depicts the device (top) after it has been brought into close proximity to the storage plate (bottom). The pins of the device are in contact with the fluid in the wells of the storage plate.
Figure 9C:
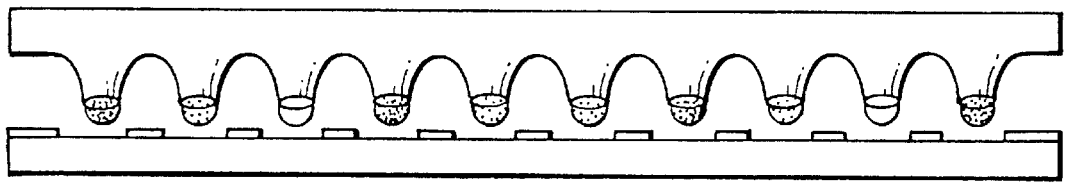
FIG. 9C depicts the device after it has been moved away from the storage plate and is being moved downward into close proximity to an assay plate. Fluid has been picked up from the storage plate by the pins of the device and is about to be transferred to the assay plate.
Figure 9D:
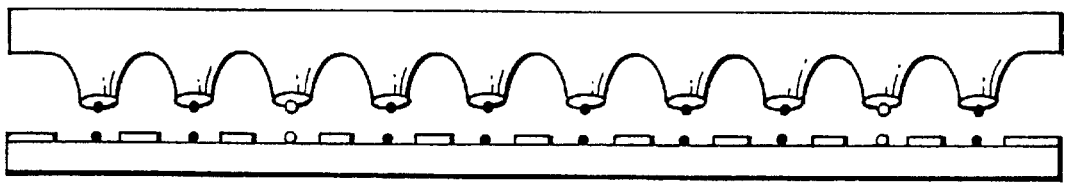
FIG. 9D depicts the device after it has been moved out of close proximity to the assay plate, thus transferring fluid from the pins of the device into the wells of the assay plate. The device is now being moved away from the assay plate. The spatial array of different fluids in the wells of the storage plate has been recreated in the wells of the assay plate.
Figure 9E:
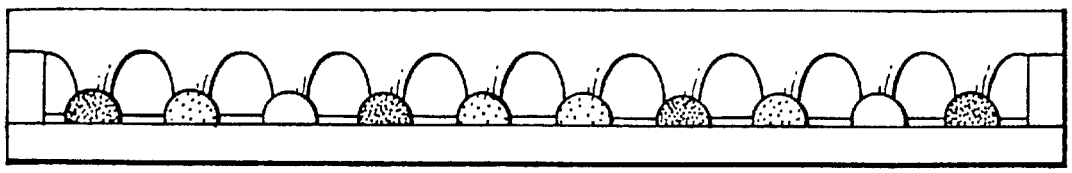
FIG. 9E shows the device after it has been returned to the storage plate, where it acts as a cover.

FIGS. 7A–B shows the results of additional experiments that demonstrate that cooling the surface of a slide to the dew point can result in substantially increasing the time for a sample on the slide to evaporate.

EXAMPLE 4

DMSO, labeled with a known concentration of $^{33}$P-ATP, and present in a spatial array in virtual wells, was spotted onto glass slides using devices having pins that were made of gold coated tungsten wire. The diameter of the pins was varied in order to determine the effect of varying the diameter on the amount of fluid transferred. The device was manipulated by hand. The results are shown in Table 5.

TABLE 5

| SAMPLE | ERROR (%) | COUNTS |
|---|---|---|
| 1 | 0.83 | 58,166 |
| 2 | 0.89 | 50,375 |
| 3 | 1.17 | 29,036 |
| 4 | 1.62 | 15,254 |
| 5 | 1.96 | 10,452 |
| 6 | 2.16 | 8,551 |
| 7 | 5.26 | 1,446 |
| 8 | 8.28 | 583 |
| 9 | 4.46 | 2,015 |
| 10 | 4.56 | 1,923 |
| 11 | 4.15 | 2,325 |
| 12 | 5.72 | 1,224 |
| 13 | 5.82 | 1,179 |
| 14 | 5.26 | 1,445 |
| 15 | 7.14 | 784 |
| 16 | 4.95 | 1,632 |
| 17 | 6.49 | 949 |
| 18 | 6.25 | 1,024 |
| 19 | 5.30 | 1,426 |
| 20 | 6.08 | 1,081 |
| 21 | 6.39 | 980 |
| 22 | 7.02 | 811 |
| 23 | 6.38 | 983 |
| 24 | 6.23 | 1,030 |
| 25 | 5.66 | 1,247 |
| 26 | 5.77 | 1,203 |
| 27 | 89.44 | 5 |
| 28 | 53.45 | 14 |
| 29 | 57.74 | 12 |
| 30 | 60.30 | 11 |
| 31 | 60.30 | 11 |
| 32 | 16.90 | 140 |
| 33 | 14.21 | 198 |
| 34 | 16.61 | 145 |
| 35 | 18.49 | 117 |
| 36 | 17.54 | 130 |
| 37 | 17.34 | 133 |
| 38 | 20.74 | 93 |
| 39 | 19.80 | 102 |
| 40 | 17.28 | 134 |
| 41 | 22.22 | 81 |
| 42 | 15.76 | 161 |
| 43 | 18.03 | 123 |
| 44 | 15.03 | 177 |
| 45 | 15.12 | 175 |
| 46 | 16.55 | 146 |
| 47 | 19.16 | 109 |
| 48 | 16.78 | 142 |
| 49 | 16.50 | 147 |
| 50 | 17.96 | 124 |
| 51 | 16.22 | 152 |
| 52 | 20.97 | 91 |
| 53 | 18.81 | 113 |
| 54 | 18.03 | 123 |
| 55 | 18.65 | 115 |
| 56 | 22.09 | 82 |
| 57 | 14.91 | 180 |
| 58 | 22.79 | 77 |
| 59 | 28.57 | 49 |
| 60 | 81.65 | 6 |
| 61 | 75.59 | 7 |
| 62 | 81.65 | 6 |
| 63 | 50.00 | 16 |
| 64 | 60.30 | 11 |

Figure 10:
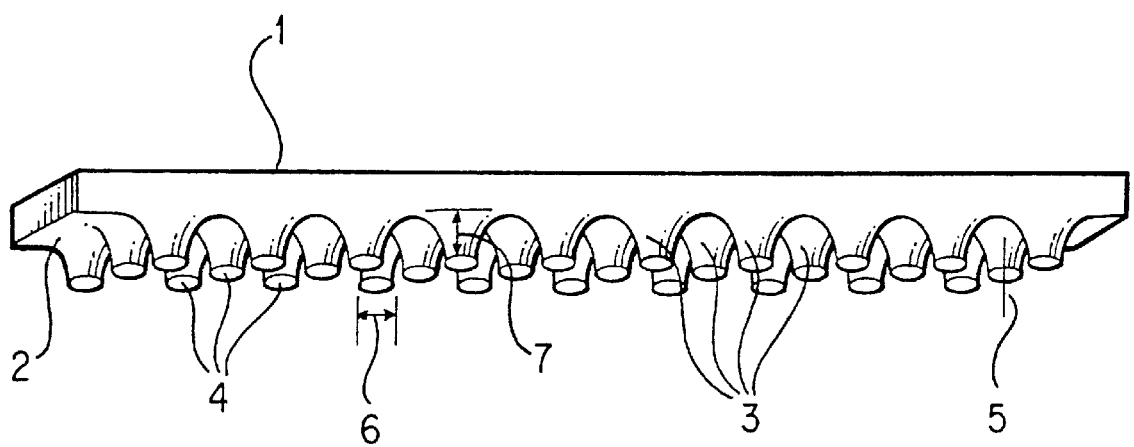
FIG. 10 illustrates a portion of a typical device of the present invention. The device has a base 1 having a generally flat surface 2 to which are attached a plurality of pins 3. The pins 3 are generally cylindrical projections from the surface 2 having faces 4 which are parallel to the suface 2 and in which the longitutidinal axis 5 of the pins is perpendicular to the surface 2. The faces 4 are flat, generally closed polygons or circular portions having a diameter 6. The pin has a depth 7, which is determined by the amount of undercutting made by the microetching process that cuts out the pins; or by the machining height for a machined device such as one made by wire EDM; or by the the mold depth for a molded device. Not shown is the edge of the plate that allows this piece to act as a self aligning cover for storage and insures alignment during transfer.
Figure 11A:
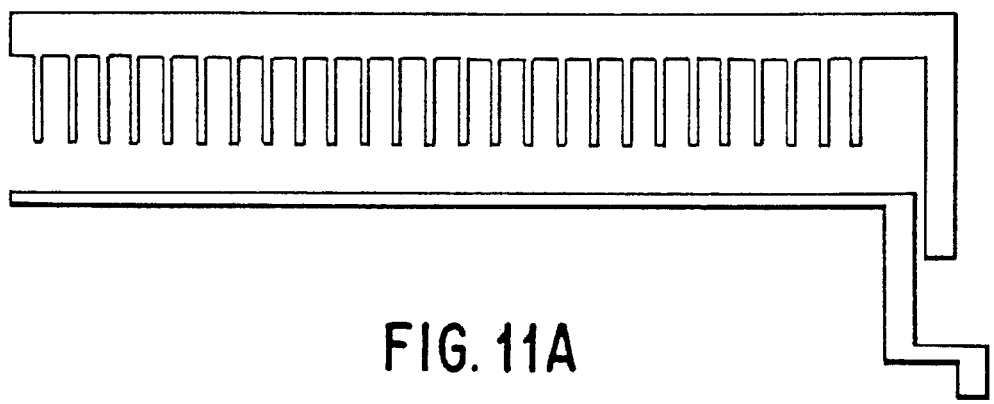
FIGS. 11A–D shows pins that have been treated to produce hydrophilic tips and a hydrophobic shaft.
Figure 11B:
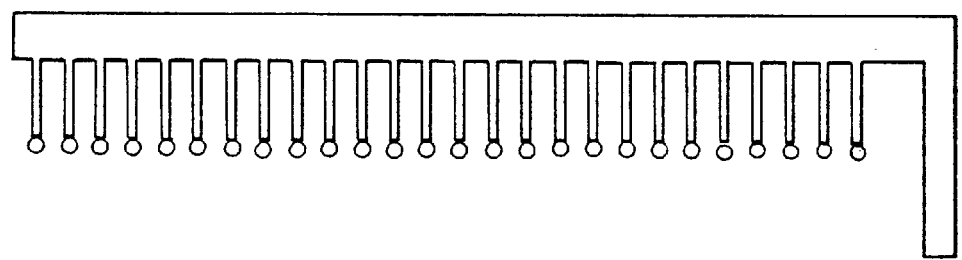
Figure 11C:
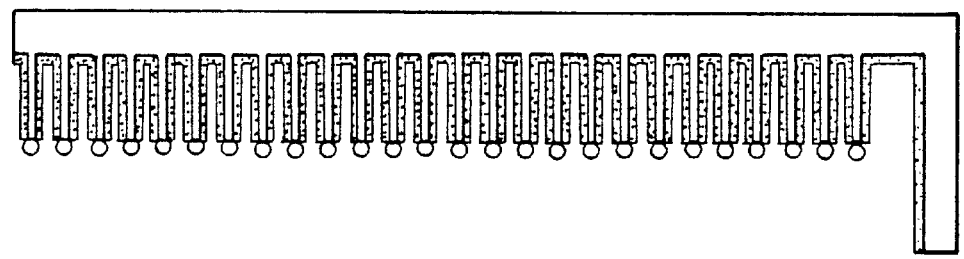
Figure 11D:
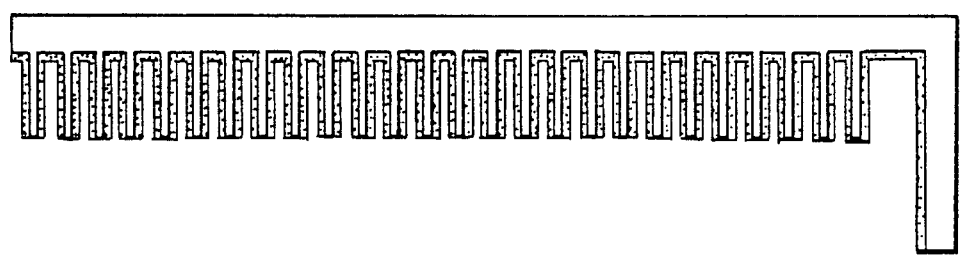

Items 1 to 6 are control samples that were produced by pipetting known volumes onto the slide. Items 7 to 26 are samples spotted using four different each having pins made from a different length of 20 mil o.d gold coated wire, i.e., the pins on each device had a different depth (see FIG. 10).

Items 27 to 31 and 60 to 64 are background controls. Items 32 to 59 are samples spotted using five different devices, each having pins made from a different length of 10 mil o.d gold coated tungsten wire, i.e., the pins on each device had a different depth (see FIG. 10).

The results of Table 5 show that spotting is fairly reproducible, i.e., within the error of the counts. Also, the 20 mil o.d. diameter wire pins (which have a face diameter of about 500 $\mu$m) transfer about 20 nl. Thus, it can be concluded that in order to transfer 10 nl of fluid, one should use pins that have faces with diameters of about 300 $\mu$m to 400 $\mu$m.

EXAMPLE 5

Assay for PTP-1b Inhibition using Plates Containing Virtual Wells

First, 5 nl of differing concentrations of the PTP-1b inhibitor L783,016 were spotted from 1 $\mu$reservoirs on a virtual well plate to a clean virtual well plate by the use of pins on the BioMek 2000. Next, the plate with compounds and a second plate were put on cold blocks on the Cartesian PixSys pipetter stage and chilled to the dew point to prevent evaporation. 600 nl of the substrate in buffer was added to each well of the compound containing plate and 400 nl of the enzyme in buffer was added to each well of the other palte. The two plates were sandwiched with a spacer and allowed to incubate for up to 72 hours in a humidified chamber at room temperature. The data shown in FIG. 11 were obtained after a 75 minute incubation and readings on the Fluorimager from Molecular Dynamics. The controls were run in 100 µl in a standard microtiter plate at the same time and then 1 µl of each control was pipetted onto a second virtual well plate at the time of the read.

These data demonstrate that the use of plates containing virtual wells to run an inhibition assay produces results similar to those obtained when the assay is run in conventional microtiter plates.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A microtiter-like plate comprising:
    a bottom having an upper surface comprising a plurality of virtual wells, said virtual wells being relatively hydrophillic domains within a relatively hydrophobic field; and
    a cover or top configured for enclosing said bottom, wherein said cover or top has a lower surface comprising a plurality of virtual wells, and said plurality of virtual wells of said bottom and said top are present in an arrangement such that, when said bottom and said top are in close proximity, column-like fluid wells are formed between said bottom and said top, or fluid is transferred, or components are captured.

2. The microtiter-like plate of claim 1 where said bottom comprises a sidewall or spacer and said top rests on said sidewall or spacer.

3. The microtiter-like plate of claim 2 where said top has a sidewall and the difference in the height of said sidewall of said bottom and said sidewall of said top is such that when said top is resting on said bottom sidewall, then said upper surface of said bottom and said lower surface of said top are in close proximity.

4. The microtiter-like plate of claim 1 comprising a spacer that can vary in height so that the distance between said bottom and said top is determined by the height of said spacer.

5. The microtiter-like plate of claim 1 where said hydrophilic domains are selected from the group consisting of: plain glass; derivatized glass; silanized glass; glass with bio- and non-biopolymers absorbed; polystyrene or other plastics; Indium Tin Oxide or other metal oxides; gold or other metals; silicon or other crystals; and ceramics.

6. The microtiter-like plate of claim 1 where said hydrophilic domains are polygons or circles having a diameter of from about 10 µm to about 10 mm.

7. The microtiter-like plate of claim 1 where said hydrophobic field is selected from the group consisting of: polyfluorocarbons; TEFLON® or TEFLON® beads; perfluoropropene; paraffin or other waxes or oils; polyethylene or other hydrocarbons; chlorodimethyl octyl silane or other silanizing agents; polypropylene or other hydrophobic polymers; bifunctional materials containing beads or other hydrophobic protrusions such as a polyfluorocarbon or polyfluorocarbon coated beads; and hydrocarbon or hydrocarbon-coated beads.

8. The microtiter-like plate of claim 7 where said hydrophobic field is layered on a smooth or microscopically rough surface where the surface is rough to about from 50 to 5,000 nm.

9. A method of transferring fluid to a plurality of virtual wells comprising:
    (a) providing a first plate or lid comprising a plurality of virtual wells to which said fluid is to be transferred;
    (b) providing a second plate or lid on which said fluid is present;
    (c) moving said first plate or lid and said second plate or lid into close proximity so that fluid is transferred from said second plate or lid to said plurality of virtual wells of said first plate or lid.

10. A method of adding fluid to a plurality of virtual wells comprising:
    a) providing a plate or lid containing a plurality of virtual wells to which said fluid is to be added;
    b) moving said plate or lid into close proximity to a fluid reservoir so that fluid is added to said plurality of virtual wells of said plate or lid from said reservoir; and
    c) shaking said plate or lid.

11. A method of nearly simultaneously adding fluid to a plurality of virtual wells so as to enable detection of flash reagents or to enable kinetic studies comprising:
    (a) providing a plate or lid containing a plurality of virtual wells to which said fluid is to be added;
    (b) providing a second plate or lid on which said fluid is present;
    (c) moving said first plate or lid and said second plate or lid into close proximity so that all or most of the fluid is transferred from said second plate or lid simultaneously or nearly simultaneously to said plurality of virtual wells of said first plate or mixed with fluid already in said first plate or lid.

12. The method of claim 11 where step (c) is practiced while said first plate is in front of a detector.

13. A method of removing fluid from a plurality of virtual wells comprising:
    (a) providing a first plate or lid comprising a plurality of virtual wells in which said fluid is present;
    (b) providing a second plate or lid onto which said fluid is to be transferred;
    (c) moving said first plate or lid and said second plate or lid into close proximity so that fluid is transferred from said plurality of virtual wells of said first plate or lid to said second plate or lid, thus removing some or all of said fluid from said virtual wells of said first plate or lid.

14. A method for limiting evaporation in a microtiter-like plate containing virtual wells during incubation with a lid comprising providing a fluid reservoir in the plate so that any gas that moves into the plate is humidified before it reaches the virtual wells.

15. A method of screening using a microtiter-like plate having a top and bottom comprising:
    a) adding a series of reagents to a plurality of virtual wells in a microtiter-like plate;
    b) adding a spatially defined array of compounds to the plurality of virtual wells before or after (a);
    c) moving said top into close proximity with said bottom so that column-like fluid wells are formed between said bottom and said top, or fluid is transferred, or components are captured;

d) incubating the reagents and compound; and e) reading a diagnostic signal from the virtual wells.

16. The method of claim 15 where the total volume in the virtual wells after step (b) is about 100 nl to about 10 µl.

17. The method of claim 15 where the method furthermore comprises, after step d) and before step e), the additional steps of:

(i) separating the top and bottom of the microtiter-like plate and adding a new top or bottom that is engineered to bind one or more of the reagents in the virtual wells;

(ii) incubating as desired to allow binding of the reagents to the new top or bottom;

(iii) washing the bound reagents as desired;

(iv) repeating steps (a)–(b) and (i)–(iii) above as desired.

18. The method of claim 15 comprising repeating step (d) one or more times.

19. A method of screening to identify a compound capable of modulating a preselected biological activity exhibited by cells comprising:

(a) providing cells in the virtual wells of a microtiter-like plate, said microtiter-like plate comprising a top and bottom, and a sidewall or spacer that vary in height so that the distance between said bottom and said top is determined by the height of said sidewall or spacer;

(b) exposing the cells to a compound or collection of compounds suspected of being capable of modulating the preselected biological activity to be exhibited by the cells; and (c) determining whether the preselected biological activity has been modulated.

20. The method of claim 19 where the preselected biological activity is selected from the group consisting of: changes in membrane potential of the cells; increases or decreases in metabolites or ions such as ATP, cAMP, cGMP, phospholipids, calcium; changes in the transcription of certain genes; changes in fluorescent or chemiluminescent behaviour; changes in pH; changes in enzymatic activity; changes in the activity of receptor proteins; changes in the activity of ion channels; changes in the translational control of certain mRNAs; changes in the translocation of certain proteins into or out of subcellular locations; cell growth or inhibition of growth; pigment dispersion or aggregation; and antibody binding.

21. A method of high throughput screening to identify a substance capable of binding to or modulating the activity of a protein or nucleic acid comprising:

(a) providing on a first plate or lid said protein or said nucleic acid, in solution, in membranes, or in cells, in virtual wells;

(b) exposing said protein or said nucleic acid to a substance suspected of being capable of binding to or modulating the activity of said protein or said nucleic acid by moving a second plate or lid in close proximity with said first plate or lid, said second plate or lid having said substance disposed thereon; and (c) determining whether said substance modulates the activity of said protein or said nucleic acid.

* * * * *